US006639129B2

(12) United States Patent
ffrench-Constant et al.

(10) Patent No.: US 6,639,129 B2
(45) Date of Patent: Oct. 28, 2003

(54) **DNA SEQUENCES FROM *PHOTORHABDUS LUMINESCENS***

(75) Inventors: Richard H. ffrench-Constant, Bath (GB); David J. Bowen, Oregon, WI (US); Thomas A. Rocheleau, Madison, WI (US); Nicholas R. Waterfield, Bath (GB)

(73) Assignees: Wisconsin Alumni Research Foundation, Madison, WI (US); University of Bath, Bath (GB)

( * ) Notice: Subject to any disclaimer, the term of this patent is extended or adjusted under 35 U.S.C. 154(b) by 0 days.

(21) Appl. No.: 09/817,514

(22) Filed: Mar. 26, 2001

(65) Prior Publication Data

US 2002/0078478 A1 Jun. 20, 2002

Related U.S. Application Data

(60) Provisional application No. 60/191,806, filed on Mar. 24, 2000.

(51) Int. Cl.[7] .......................... C12N 5/04; C12N 15/31; C12N 15/82; A01H 5/00; A01H 5/10

(52) U.S. Cl. ....................... 800/302; 800/278; 800/298; 800/295; 800/317.1; 800/317.2; 800/288; 800/320; 800/320.1; 800/320.2; 800/314; 536/23.7; 536/23.1

(58) Field of Search ................................. 800/302, 278, 800/298, 295, 317.1, 317.2, 288, 320, 320.1, 320.2, 314; 536/23.7

(56) References Cited

FOREIGN PATENT DOCUMENTS

| | | |
|---|---|---|
| WO | WO98/08932 | 3/1998 |
| WO | WO01/11029 | 2/2001 |

OTHER PUBLICATIONS

Morgan, J. Alun et al., "Cloning and expression of insecticidal toxin genes from Xenorhabdus species", SIP 1999 Program & Asbstracts, XXXII Meeting, University of California at Irvine, Aug. 22–27, 1999.

Morgan, J Alun W., et al., Sequence Analysis of Insecticidal Genes from *Xenorhabdus nematophilus* PMF1296, Applied and Environmental Microbiology, 67: 2062–2069 (May 2001).

*Primary Examiner*—Elizabeth F. McElwain
*Assistant Examiner*—Medina A. Ibrahim
(74) *Attorney, Agent, or Firm*—Donald R. Stuart

(57) ABSTRACT

Nucleotide sequences for two genes, tcdB and tccC2, from the tcd genomic region of *Photorhabdus luminescens* W-14 are useful in heterologous expression of orally active insect toxins.

11 Claims, No Drawings

SEQUENCE LISTING

```
<160> NUMBER OF SEQ ID NOS: 8

<210> SEQ ID NO 1
<211> LENGTH: 7551
<212> TYPE: DNA
<213> ORGANISM: Photorhabdus luminescens

<400> SEQUENCE: 1

atgaacgagt ctgtaaaaga gatacctgat gtattaaaaa gccagtgtgg ttttaattgt      60

ctgacagata ttagccacag ctcttttaat gaatttcgcc agcaagtatc tgagcacctc     120

tcctggtccg aaacacacga cttatatcat gatgcacaac aggcacaaaa ggataatcgc     180

ctgtatgaag cgcgtattct caaacgcgcc aatccccaat tacaaaatgc ggtgcatctt     240

gccattctcg ctcccaatgc tgaactgata ggctataaca atcaatttag cggtagagcc     300

agtcaatatg ttgcgccggg taccgtttct tccatgttct cccccgccgc ttatttgact     360

gaactttatc gtgaagcacg caatttacac gcaagtgact ccgtttatta tctggatacc     420

cgccgcccag atctcaaatc aatggcgctc agtcagcaaa atatggatat agaattatcc     480
```

-continued

```
acactctctt tgtccaatga gctgttattg gaaagcatta aaactgaatc taaactggaa    540

aactatacta aagtgatgga aatgctctcc actttccgtc cttccggcgc aacgccttat    600

catgatgctt atgaaaatgt gcgtgaagtt atccagctac aagatcctgg acttgagcaa    660

ctcaatgcat caccggcaat tgccgggttg atgcatcaag cctccctatt gggtattaac    720

gcttcaatct cgcctgagct atttaatatt ctgacggagg agattaccga aggtaatgct    780

gaggaacttt ataagaaaaa ttttggtaat atcgaaccgg cctcattggc tatgccggaa    840

taccttaaac gttattataa tttaagcgat gaagaactta gtcagtttat tggtaaagcc    900

agcaattttg gtcaacagga atatagtaat aaccaactta ttactccggt agtcaacagc    960

agtgatggca cggttaaggt atatcggatc acccgcgaat atacaaccaa tgcttatcaa   1020

atggatgtgg agctatttcc cttcggtggt gagaattatc ggttagatta taaattcaaa   1080

aatttttata atgcctctta tttatccatc aagttaaatg ataaaagaga acttgttcga   1140

actgaaggcg ctcctcaagt caatatagaa tactccgcaa atatcacatt aaataccgct   1200

gatatcagtc aacctttga aattggcctg acacgagtac ttccttccgg ttcttgggca   1260

tatgccgccg caaaatttac cgttgaagag tataaccaat actcttttct gctaaaactt   1320

aacaaggcta ttcgtctatc acgtgcgaca gaattgtcac ccacgattct ggaaggcatt   1380

gtgcgcagtg ttaatctaca actggatatc aacacagacg tattaggtaa agtttttctg   1440

actaaatatt atatgcagcg ttatgctatt catgctgaaa ctgccctgat actatgcaac   1500

gcgcctattt cacaacgttc atatgataat caacctagcc aatttgatcg cctgtttaat   1560

acgccattac tgaacggaca atatttttct accggcgatg aggagattga tttaaattca   1620

ggtagcaccg gcgattggcg aaaaaccata cttaagcgtg catttaatat tgatgatgtc   1680

tcgctcttcc gcctgcttaa aattaccgac catgataata aagatggaaa aattaaaaat   1740

aacctaaaga atctttccaa tttatatatt ggaaaattac tggcagatat tcatcaatta   1800

accattgatg aactggattt attactgatt gccgtaggtg aaggaaaaac taatttatcc   1860

gctatcagtg ataagcaatt ggctaccctg atcagaaaac tcaatactat taccagctgg   1920

ctacatacac agaagtggag tgtattccag ctatttatca tgacctccac cagctataac   1980

aaaacgctaa cgcctgaaat taagaatttg ctggataccg tctaccacgg tttacaaggt   2040

tttgataaag acaaagcaga tttgctacat gtcatggcgc cctatattgc ggccaccttg   2100

caattatcat cggaaaatgt cgcccactcg gtactccttt gggcagataa gttacagccc   2160

ggcgacggcg caatgacagc agaaaaattc tgggactggt tgaatactaa gtatacgccg   2220

ggttcatcgg aagccgtaga aacgcaggaa catatcgttc agtattgtca ggctctggca   2280

caattggaaa tggtttacca ttccaccggc atcaacgaaa acgccttccg tctatttgtg   2340

acaaaaccag agatgtttgg cgctgcaact ggagcagcgc ccgcgcatga tgccctttca   2400

ctgattatgc tgacacgttt tgcggattgg gtgaacgcac taggcgaaaa agcgtcctcg   2460

gtgctagcgg catttgaagc taactcgtta acggcagaac aactggctga tgccatgaat   2520

cttgatgcta atttgctgtt gcaagccagt attcaagcac aaaatcatca acatcttccc   2580

ccagtaactc cagaaaatgc gttctcctgt tggacatcta tcaatactat cctgcaatgg   2640

gttaatgtcg cacaacaatt gaatgtcgcc ccacagggcg tttccgcttt ggtcgggctg   2700

gattatattc aatcaatgaa agagacaccg acctatgccc agtgggaaaa cgcggcaggc   2760

gtattaaccg ccgggttgaa ttcacaacag gctaatacat tacacgcttt tctggatgaa   2820

tctcgcagtg ccgcattaag cacctactat atccgtcaag tcgccaaggc agcggcggct   2880
```

-continued

```
attaaaagcc gtgatgactt gtatcaatac ttactgattg ataatcaggt ttctgcggca   2940
ataaaaacca cccggatcgc cgaagccatt gccagtattc aactgtacgt caaccgggca   3000
ttggaaaatg tggaagaaaa tgccaattcg gggttatca  gccgccaatt ctttatcgac   3060
tgggacaaat acaataaacg ctacagcact tgggcgggtg tttctcaatt agtttactac   3120
ccggaaaact atattgatcc gaccatgcgt atcggacaaa ccaaaatgat ggacgcatta   3180
ctgcaatccg tcagccaaag ccaattaaac gccgataccg tcgaagatgc ctttatgtct   3240
tatctgacat cgtttgaaca agtggctaat cttaaagtta ttagcgcata tcacgataat   3300
attaataacg atcaagggct gacctatttt atcggactca gtgaaactga tgccggtgaa   3360
tattattggc gcagtgtcga tcacagtaaa ttcaacgacg gtaaattcgc ggctaatgcc   3420
tggagtgaat ggcataaaat tgattgtcca attaaccctt ataaaagcac tatccgtcca   3480
gtgatatata aatcccgcct gtatctgctc tggttggaac aaaaggagat caccaaacag   3540
acaggaaata gtaaagatgg ctatcaaact gaaacggatt atcgttatga actaaaattg   3600
gcgcatatcc gctatgatgg cacttggaat acgccaatca cctttgatgt caataaaaaa   3660
atatccgagc taaaactgga aaaaaataga gcgcccggac tctattgtgc cggttatcaa   3720
ggtgaagata cgttgctggt gatgttttat aaccaacaag acacactaga tagttataaa   3780
aacgcttcaa tgcaaggact atatatcttt gctgatatgg catccaaaga tatgacccca   3840
gaacagagca atgtttatcg ggataatagc tatcaacaat ttgataccaa taatgtcaga   3900
agagtgaata accgctatgc agaggattat gagattcctt cctcggtaag tagccgtaaa   3960
gactatggtt ggggagatta ttacctcagc atggtatata acggagatat tccaactatc   4020
aattacaaag ccgcatcaag tgatttaaaa atctatatct caccaaaatt aagaattatt   4080
cataatggat atgaaggaca gaagcgcaat caatgcaatc tgatgaataa atatggcaaa   4140
ctaggtgata aatttattgt ttatactagc ttgggggtca atccaaataa ctcgtcaaat   4200
aagctcatgt tttaccccgt ctatcaatat agcggaaaca ccagtggact caatcaaggg   4260
agactactat tccaccgtga caccacttat ccatctaaag tagaagcttg gattcctgga   4320
gcaaaacgtt ctctaaccaa ccaaaatgcc gccattggtg atgattatgc tacagactct   4380
ctgaataaac cggatgatct taagcaatat atctttatga ctgacagtaa agggactgct   4440
actgatgtct caggcccagt agagattaat actgcaattt ctccagcaaa agttcagata   4500
atagtcaaag cgggtggcaa ggagcaaact tttaccgcag ataaagatgt ctccattcag   4560
ccatcaccta gctttgatga aatgaattat caatttaatg cccttgaaat agacggttct   4620
ggtctgaatt ttattaacaa ctcagccagt attgatgtta cttttaccgc atttgcggag   4680
gatggccgca aactgggtta tgaaagtttc agtattcctg ttaccctcaa ggtaagtacc   4740
gataatgccc tgaccctgca ccataatgaa aatggtgcgc aatatatgca atggcaatcc   4800
tatcgtaccc gcctgaatac tctatttgcc cgccagttgg ttgcacgcgc caccaccgga   4860
atcgatacaa ttctgagtat ggaaactcag aatattcagg aaccgcagtt aggcaaaggt   4920
ttctatgcta cgttcgtgat acctccctat aacctatcaa ctcatggtga tgaacgttgg   4980
tttaagcttt atatcaaaca tgttgttgat aataattcac atattatcta ttcaggccag   5040
ctaacagata caaatataaa catcacatta tttattcctc ttgatgatgt cccattgaat   5100
caagattatc acgccaaggt ttatatgacc ttcaagaaat caccatcaga tggtacctgg   5160
tggggccctc actttgttag agatgataaa ggaatagtaa caataaaccc taaatccatt   5220
```

-continued

```
ttgacccatt ttgagagcgt caatgtcctg aataatatta gtagcgaacc aatggatttc   5280

agcggcgcta acagcctcta tttctgggaa ctgttctact ataccccgat gctggttgct   5340

caacgtttgc tgcatgaaca gaacttcgat gaagccaacc gttggctgaa atatgtctgg   5400

agtccatccg gttatattgt ccacggccag attcagaact accagtggaa cgtccgcccg   5460

ttactggaag acaccagttg gaacagtgat cctttggatt ccgtcgatcc tgacgcggta   5520

gcacagcacg atccaatgca ctacaaagtt tcaactttta tgcgtacctt ggatctattg   5580

atagcacgcg gcgaccatgc ttatcgccaa ctggaacgag atacactcaa cgaagcgaag   5640

atgtggtata tgcaagcgct gcatctatta ggtgacaaac cttatctacc gctgagtacg   5700

acatggagtg atccacgact agacagagcc gcggatatca ctacccaaaa tgctcacgac   5760

agcgcaatag tcgctctgcg gcagaatata cctacaccgg cacctttatc attgcgcagc   5820

gctaataccc tgactgatct cttcctgccg caaatcaatg aagtgatgat gaattactgg   5880

cagacattag ctcagagagt atacaatctg cgtcataacc tctctatcga cggccagccg   5940

ttatatctgc caatctatgc cacaccggcc gatccgaaag cgttactcag cgccgccgtt   6000

gccacttctc aaggtggagg caagctaccg gaatcattta tgtccctgtg gcgtttcccg   6060

cacatgctgg aaaatgcgcg cggcatggtt agccagctca cccagttcgg ctccacgtta   6120

caaaatatta tcgaacgtca ggacgcggaa gcgctcaatg cgttattaca aaatcaggcc   6180

gccgagctga tattgactaa cctgagcatt caggacaaaa ccattgaaga attggatgcc   6240

gagaaaacgg tgttggaaaa atccaaagcg ggagcacaat cgcgctttga tagctacggc   6300

aaactgtacg atgagaatat caacgccggt gaaaaccaag ccatgacgct acgagcgtcc   6360

gccgccgggc ttaccacggc agttcaggca tcccgtctgg ccggtgcggc ggctgatctg   6420

gtgcctaaca tcttcggctt tgccggtggc ggcagccgtt ggggggctat cgctgaggcg   6480

acaggttatg tgatggaatt ctccgcgaat gttatgaaca ccgaagcgga taaaattagc   6540

caatctgaaa cctaccgtcg tcgccgtcag gagtgggaga tccagcggaa taatgccgaa   6600

gcggaattga agcaaatcga tgctcagctc aaatcactcg ctgtacgccg cgaagccgcc   6660

gtattgcaga aaaccagtct gaaaacccaa caagaacaga cccaatctca attggccttc   6720

ctgcaacgta agttcagcaa tcaggcgtta tacaactggc tgcgtggtcg actggcggcg   6780

atttacttcc agttctacga tttggccgtc gcgcgttgcc tgatggcaga acaagcttac   6840

cgttgggaac tcaatgatga ctctgcccgc ttcattaaac cgggcgcctg gcagggaacc   6900

tatgccggtc tgcttgcagg tgaaaccttg atgctgagtc tggcacaaat ggaagacgct   6960

catctgaaac gcgataaacg cgcattagag gttgaacgca cagtatcgct ggccgaagtt   7020

tatgcaggat taccaaaaga taacggtcca ttttccctgg ctcaggaaat tgacaagctg   7080

gtgagtcaag gttcaggcag tgccggcagt ggtaataata atttggcgtt cggcgccggc   7140

acggacacta aaacctcttt gcaggcatca gtttcattcg ctgatttgaa aattcgtgaa   7200

gattacccgg catcgcttgg caaaattcga cgtatcaaac agatcagcgt cactttgccc   7260

gcgctactgg gaccgtatca ggatgtacag gcaatattgt cttacggcga taaagccgga   7320

ttagctaacg gctgtgaagc gctggcagtt tctcacggta tgaatgacag cggccaattc   7380

cagctcgatt tcaacgatgg caaattcctg ccattcgaag gcatcgccat tgatcaaggc   7440

acgctgacac tgagcttccc aaatgcatct atgccggaga aaggtaaaca agccactatg   7500

ttaaaaaccc tgaacgatat cattttgcat attcgctaca ccattaaata a            7551
```

-continued

<210> SEQ ID NO 2
<211> LENGTH: 2516
<212> TYPE: PRT
<213> ORGANISM: Photorhabdus luminescens

<400> SEQUENCE: 2

```
Met Asn Glu Ser Val Lys Glu Ile Pro Asp Val Leu Lys Ser Gln Cys
1               5                   10                  15

Gly Phe Asn Cys Leu Thr Asp Ile Ser His Ser Ser Phe Asn Glu Phe
            20                  25                  30

Arg Gln Gln Val Ser Glu His Leu Ser Trp Ser Glu Thr His Asp Leu
        35                  40                  45

Tyr His Asp Ala Gln Gln Ala Gln Lys Asp Asn Arg Leu Tyr Glu Ala
    50                  55                  60

Arg Ile Leu Lys Arg Ala Asn Pro Gln Leu Gln Asn Ala Val His Leu
65                  70                  75                  80

Ala Ile Leu Ala Pro Asn Ala Glu Leu Ile Gly Tyr Asn Asn Gln Phe
                85                  90                  95

Ser Gly Arg Ala Ser Gln Tyr Val Ala Pro Gly Thr Val Ser Ser Met
            100                 105                 110

Phe Ser Pro Ala Ala Tyr Leu Thr Glu Leu Tyr Arg Glu Ala Arg Asn
        115                 120                 125

Leu His Ala Ser Asp Ser Val Tyr Tyr Leu Asp Thr Arg Arg Pro Asp
    130                 135                 140

Leu Lys Ser Met Ala Leu Ser Gln Gln Asn Met Asp Ile Glu Leu Ser
145                 150                 155                 160

Thr Leu Ser Leu Ser Asn Glu Leu Leu Leu Glu Ser Ile Lys Thr Glu
                165                 170                 175

Ser Lys Leu Glu Asn Tyr Thr Lys Val Met Glu Met Leu Ser Thr Phe
            180                 185                 190

Arg Pro Ser Gly Ala Thr Pro Tyr His Asp Ala Tyr Glu Asn Val Arg
        195                 200                 205

Glu Val Ile Gln Leu Gln Asp Pro Gly Leu Glu Gln Leu Asn Ala Ser
    210                 215                 220

Pro Ala Ile Ala Gly Leu Met His Gln Ala Ser Leu Leu Gly Ile Asn
225                 230                 235                 240

Ala Ser Ile Ser Pro Glu Leu Phe Asn Ile Leu Thr Glu Glu Ile Thr
                245                 250                 255

Glu Gly Asn Ala Glu Glu Leu Tyr Lys Lys Asn Phe Gly Asn Ile Glu
            260                 265                 270

Pro Ala Ser Leu Ala Met Pro Glu Tyr Leu Lys Arg Tyr Tyr Asn Leu
        275                 280                 285

Ser Asp Glu Glu Leu Ser Gln Phe Ile Gly Lys Ala Ser Asn Phe Gly
    290                 295                 300

Gln Gln Glu Tyr Ser Asn Asn Gln Leu Ile Thr Pro Val Val Asn Ser
305                 310                 315                 320

Ser Asp Gly Thr Val Lys Val Tyr Arg Ile Thr Arg Glu Tyr Thr Thr
                325                 330                 335

Asn Ala Tyr Gln Met Asp Val Glu Leu Phe Pro Phe Gly Gly Glu Asn
            340                 345                 350

Tyr Arg Leu Asp Tyr Lys Phe Lys Asn Phe Tyr Asn Ala Ser Tyr Leu
        355                 360                 365

Ser Ile Lys Leu Asn Asp Lys Arg Glu Leu Val Arg Thr Glu Gly Ala
    370                 375                 380
```

-continued

```
Pro Gln Val Asn Ile Glu Tyr Ser Ala Asn Ile Thr Leu Asn Thr Ala
385                 390                 395                 400

Asp Ile Ser Gln Pro Phe Glu Ile Gly Leu Thr Arg Val Leu Pro Ser
                405                 410                 415

Gly Ser Trp Ala Tyr Ala Ala Ala Lys Phe Thr Val Glu Glu Tyr Asn
            420                 425                 430

Gln Tyr Ser Phe Leu Leu Lys Leu Asn Lys Ala Ile Arg Leu Ser Arg
        435                 440                 445

Ala Thr Glu Leu Ser Pro Thr Ile Leu Glu Gly Ile Val Arg Ser Val
    450                 455                 460

Asn Leu Gln Leu Asp Ile Asn Thr Asp Val Leu Gly Lys Val Phe Leu
465                 470                 475                 480

Thr Lys Tyr Tyr Met Gln Arg Tyr Ala Ile His Ala Glu Thr Ala Leu
                485                 490                 495

Ile Leu Cys Asn Ala Pro Ile Ser Gln Arg Ser Tyr Asp Asn Gln Pro
            500                 505                 510

Ser Gln Phe Asp Arg Leu Phe Asn Thr Pro Leu Leu Asn Gly Gln Tyr
        515                 520                 525

Phe Ser Thr Gly Asp Glu Glu Ile Asp Leu Asn Ser Gly Ser Thr Gly
    530                 535                 540

Asp Trp Arg Lys Thr Ile Leu Lys Arg Ala Phe Asn Ile Asp Asp Val
545                 550                 555                 560

Ser Leu Phe Arg Leu Leu Lys Ile Thr Asp His Asp Asn Lys Asp Gly
                565                 570                 575

Lys Ile Lys Asn Asn Leu Lys Asn Leu Ser Asn Leu Tyr Ile Gly Lys
            580                 585                 590

Leu Leu Ala Asp Ile His Gln Leu Thr Ile Asp Glu Leu Asp Leu Leu
        595                 600                 605

Leu Ile Ala Val Gly Glu Gly Lys Thr Asn Leu Ser Ala Ile Ser Asp
    610                 615                 620

Lys Gln Leu Ala Thr Leu Ile Arg Lys Leu Asn Thr Ile Thr Ser Trp
625                 630                 635                 640

Leu His Thr Gln Lys Trp Ser Val Phe Gln Leu Phe Ile Met Thr Ser
                645                 650                 655

Thr Ser Tyr Asn Lys Thr Leu Thr Pro Glu Ile Lys Asn Leu Leu Asp
            660                 665                 670

Thr Val Tyr His Gly Leu Gln Gly Phe Asp Lys Asp Lys Ala Asp Leu
        675                 680                 685

Leu His Val Met Ala Pro Tyr Ile Ala Ala Thr Leu Gln Leu Ser Ser
    690                 695                 700

Glu Asn Val Ala His Ser Val Leu Leu Trp Ala Asp Lys Leu Gln Pro
705                 710                 715                 720

Gly Asp Gly Ala Met Thr Ala Glu Lys Phe Trp Asp Trp Leu Asn Thr
                725                 730                 735

Lys Tyr Thr Pro Gly Ser Ser Glu Ala Val Glu Thr Gln Glu His Ile
            740                 745                 750

Val Gln Tyr Cys Gln Ala Leu Ala Gln Leu Glu Met Val Tyr His Ser
        755                 760                 765

Thr Gly Ile Asn Glu Asn Ala Phe Arg Leu Phe Val Thr Lys Pro Glu
    770                 775                 780

Met Phe Gly Ala Ala Thr Gly Ala Ala Pro Ala His Asp Ala Leu Ser
785                 790                 795                 800

Leu Ile Met Leu Thr Arg Phe Ala Asp Trp Val Asn Ala Leu Gly Glu
```

-continued

```
            805                 810                 815

Lys Ala Ser Ser Val Leu Ala Ala Phe Glu Ala Asn Ser Leu Thr Ala
            820                 825                 830

Glu Gln Leu Ala Asp Ala Met Asn Leu Asp Ala Asn Leu Leu Leu Gln
        835                 840                 845

Ala Ser Ile Gln Ala Gln Asn His Gln His Leu Pro Pro Val Thr Pro
    850                 855                 860

Glu Asn Ala Phe Ser Cys Trp Thr Ser Ile Asn Thr Ile Leu Gln Trp
865                 870                 875                 880

Val Asn Val Ala Gln Gln Leu Asn Val Ala Pro Gln Gly Val Ser Ala
                885                 890                 895

Leu Val Gly Leu Asp Tyr Ile Gln Ser Met Lys Glu Thr Pro Thr Tyr
            900                 905                 910

Ala Gln Trp Glu Asn Ala Ala Gly Val Leu Thr Ala Gly Leu Asn Ser
        915                 920                 925

Gln Gln Ala Asn Thr Leu His Ala Phe Leu Asp Glu Ser Arg Ser Ala
    930                 935                 940

Ala Leu Ser Thr Tyr Tyr Ile Arg Gln Val Ala Lys Ala Ala Ala Ala
945                 950                 955                 960

Ile Lys Ser Arg Asp Asp Leu Tyr Gln Tyr Leu Leu Ile Asp Asn Gln
                965                 970                 975

Val Ser Ala Ala Ile Lys Thr Thr Arg Ile Ala Glu Ala Ile Ala Ser
            980                 985                 990

Ile Gln Leu Tyr Val Asn Arg Ala  Leu Glu Asn Val Glu  Glu Asn Ala
        995                 1000                1005

Asn Ser  Gly Val Ile Ser Arg  Gln Phe Phe Ile Asp  Trp Asp Lys
    1010                1015                1020

Tyr Asn  Lys Arg Tyr Ser Thr  Trp Ala Gly Val Ser  Gln Leu Val
    1025                1030                1035

Tyr Tyr  Pro Glu Asn Tyr Ile  Asp Pro Thr Met Arg  Ile Gly Gln
    1040                1045                1050

Thr Lys  Met Met Asp Ala Leu  Leu Gln Ser Val Ser  Gln Ser Gln
    1055                1060                1065

Leu Asn  Ala Asp Thr Val Glu  Asp Ala Phe Met Ser  Tyr Leu Thr
    1070                1075                1080

Ser Phe  Glu Gln Val Ala Asn  Leu Lys Val Ile Ser  Ala Tyr His
    1085                1090                1095

Asp Asn  Ile Asn Asn Asp Gln  Gly Leu Thr Tyr Phe  Ile Gly Leu
    1100                1105                1110

Ser Glu  Thr Asp Ala Gly Glu  Tyr Tyr Trp Arg Ser  Val Asp His
    1115                1120                1125

Ser Lys  Phe Asn Asp Gly Lys  Phe Ala Ala Asn Ala  Trp Ser Glu
    1130                1135                1140

Trp His  Lys Ile Asp Cys Pro  Ile Asn Pro Tyr Lys  Ser Thr Ile
    1145                1150                1155

Arg Pro  Val Ile Tyr Lys Ser  Arg Leu Tyr Leu Leu  Trp Leu Glu
    1160                1165                1170

Gln Lys  Glu Ile Thr Lys Gln  Thr Gly Asn Ser Lys  Asp Gly Tyr
    1175                1180                1185

Gln Thr  Glu Thr Asp Tyr Arg  Tyr Glu Leu Lys Leu  Ala His Ile
    1190                1195                1200

Arg Tyr  Asp Gly Thr Trp Asn  Thr Pro Ile Thr Phe  Asp Val Asn
    1205                1210                1215
```

-continued

```
Lys Lys  Ile Ser Glu Leu Lys  Leu Glu Lys Asn Arg  Ala Pro Gly
    1220                 1225                 1230

Leu Tyr  Cys Ala Gly Tyr Gln  Gly Glu Asp Thr Leu  Leu Val Met
    1235                 1240                 1245

Phe Tyr  Asn Gln Gln Asp Thr  Leu Asp Ser Tyr Lys  Asn Ala Ser
    1250                 1255                 1260

Met Gln  Gly Leu Tyr Ile Phe  Ala Asp Met Ala Ser  Lys Asp Met
    1265                 1270                 1275

Thr Pro  Glu Gln Ser Asn Val  Tyr Arg Asp Asn Ser  Tyr Gln Gln
    1280                 1285                 1290

Phe Asp  Thr Asn Asn Val Arg  Arg Val Asn Asn Arg  Tyr Ala Glu
    1295                 1300                 1305

Asp Tyr  Glu Ile Pro Ser Ser  Val Ser Ser Arg Lys  Asp Tyr Gly
    1310                 1315                 1320

Trp Gly  Asp Tyr Tyr Leu Ser  Met Val Tyr Asn Gly  Asp Ile Pro
    1325                 1330                 1335

Thr Ile  Asn Tyr Lys Ala Ala  Ser Ser Asp Leu Lys  Ile Tyr Ile
    1340                 1345                 1350

Ser Pro  Lys Leu Arg Ile Ile  His Asn Gly Tyr Glu  Gly Gln Lys
    1355                 1360                 1365

Arg Asn  Gln Cys Asn Leu Met  Asn Lys Tyr Gly Lys  Leu Gly Asp
    1370                 1375                 1380

Lys Phe  Ile Val Tyr Thr Ser  Leu Gly Val Asn Pro  Asn Asn Ser
    1385                 1390                 1395

Ser Asn  Lys Leu Met Phe Tyr  Pro Val Tyr Gln Tyr  Ser Gly Asn
    1400                 1405                 1410

Thr Ser  Gly Leu Asn Gln Gly  Arg Leu Leu Phe His  Arg Asp Thr
    1415                 1420                 1425

Thr Tyr  Pro Ser Lys Val Glu  Ala Trp Ile Pro Gly  Ala Lys Arg
    1430                 1435                 1440

Ser Leu  Thr Asn Gln Asn Ala  Ala Ile Gly Asp Asp  Tyr Ala Thr
    1445                 1450                 1455

Asp Ser  Leu Asn Lys Pro Asp  Asp Leu Lys Gln Tyr  Ile Phe Met
    1460                 1465                 1470

Thr Asp  Ser Lys Gly Thr Ala  Thr Asp Val Ser Gly  Pro Val Glu
    1475                 1480                 1485

Ile Asn  Thr Ala Ile Ser Pro  Ala Lys Val Gln Ile  Ile Val Lys
    1490                 1495                 1500

Ala Gly  Gly Lys Glu Gln Thr  Phe Thr Ala Asp Lys  Asp Val Ser
    1505                 1510                 1515

Ile Gln  Pro Ser Pro Ser Phe  Asp Glu Met Asn Tyr  Gln Phe Asn
    1520                 1525                 1530

Ala Leu  Glu Ile Asp Gly Ser  Gly Leu Asn Phe Ile  Asn Asn Ser
    1535                 1540                 1545

Ala Ser  Ile Asp Val Thr Phe  Thr Ala Phe Ala Glu  Asp Gly Arg
    1550                 1555                 1560

Lys Leu  Gly Tyr Glu Ser Phe  Ser Ile Pro Val Thr  Leu Lys Val
    1565                 1570                 1575

Ser Thr  Asp Asn Ala Leu Thr  Leu His His Asn Glu  Asn Gly Ala
    1580                 1585                 1590

Gln Tyr  Met Gln Trp Gln Ser  Tyr Arg Thr Arg Leu  Asn Thr Leu
    1595                 1600                 1605
```

-continued

```
Phe Ala  Arg Gln Leu Val Ala  Arg Ala Thr Thr Gly  Ile Asp Thr
    1610                 1615                 1620

Ile Leu  Ser Met Glu Thr Gln  Asn Ile Gln Glu Pro  Gln Leu Gly
    1625                 1630                 1635

Lys Gly  Phe Tyr Ala Thr Phe  Val Ile Pro Pro Tyr  Asn Leu Ser
    1640                 1645                 1650

Thr His  Gly Asp Glu Arg Trp  Phe Lys Leu Tyr Ile  Lys His Val
    1655                 1660                 1665

Val Asp  Asn Asn Ser His Ile  Ile Tyr Ser Gly Gln  Leu Thr Asp
    1670                 1675                 1680

Thr Asn  Ile Asn Ile Thr Leu  Phe Ile Pro Leu Asp  Asp Val Pro
    1685                 1690                 1695

Leu Asn  Gln Asp Tyr His Ala  Lys Val Tyr Met Thr  Phe Lys Lys
    1700                 1705                 1710

Ser Pro  Ser Asp Gly Thr Trp  Trp Gly Pro His Phe  Val Arg Asp
    1715                 1720                 1725

Asp Lys  Gly Ile Val Thr Ile  Asn Pro Lys Ser Ile  Leu Thr His
    1730                 1735                 1740

Phe Glu  Ser Val Asn Val Leu  Asn Asn Ile Ser Ser  Glu Pro Met
    1745                 1750                 1755

Asp Phe  Ser Gly Ala Asn Ser  Leu Tyr Phe Trp Glu  Leu Phe Tyr
    1760                 1765                 1770

Tyr Thr  Pro Met Leu Val Ala  Gln Arg Leu Leu His  Glu Gln Asn
    1775                 1780                 1785

Phe Asp  Glu Ala Asn Arg Trp  Leu Lys Tyr Val Trp  Ser Pro Ser
    1790                 1795                 1800

Gly Tyr  Ile Val His Gly Gln  Ile Gln Asn Tyr Gln  Trp Asn Val
    1805                 1810                 1815

Arg Pro  Leu Leu Glu Asp Thr  Ser Trp Asn Ser Asp  Pro Leu Asp
    1820                 1825                 1830

Ser Val  Asp Pro Asp Ala Val  Ala Gln His Asp Pro  Met His Tyr
    1835                 1840                 1845

Lys Val  Ser Thr Phe Met Arg  Thr Leu Asp Leu Leu  Ile Ala Arg
    1850                 1855                 1860

Gly Asp  His Ala Tyr Arg Gln  Leu Glu Arg Asp Thr  Leu Asn Glu
    1865                 1870                 1875

Ala Lys  Met Trp Tyr Met Gln  Ala Leu His Leu Leu  Gly Asp Lys
    1880                 1885                 1890

Pro Tyr  Leu Pro Leu Ser Thr  Thr Trp Ser Asp Pro  Arg Leu Asp
    1895                 1900                 1905

Arg Ala  Ala Asp Ile Thr Thr  Gln Asn Ala His Asp  Ser Ala Ile
    1910                 1915                 1920

Val Ala  Leu Arg Gln Asn Ile  Pro Thr Pro Ala Pro  Leu Ser Leu
    1925                 1930                 1935

Arg Ser  Ala Asn Thr Leu Thr  Asp Leu Phe Leu Pro  Gln Ile Asn
    1940                 1945                 1950

Glu Val  Met Met Asn Tyr Trp  Gln Thr Leu Ala Gln  Arg Val Tyr
    1955                 1960                 1965

Asn Leu  Arg His Asn Leu Ser  Ile Asp Gly Gln Pro  Leu Tyr Leu
    1970                 1975                 1980

Pro Ile  Tyr Ala Thr Pro Ala  Asp Pro Lys Ala Leu  Leu Ser Ala
    1985                 1990                 1995

Ala Val  Ala Thr Ser Gln Gly  Gly Gly Lys Leu Pro  Glu Ser Phe
```

-continued

```
    2000                2005                2010

Met Ser  Leu Trp Arg Phe Pro  His Met Leu Glu Asn  Ala Arg Gly
    2015                2020                2025

Met Val  Ser Gln Leu Thr Gln  Phe Gly Ser Thr Leu  Gln Asn Ile
    2030                2035                2040

Ile Glu  Arg Gln Asp Ala Glu  Ala Leu Asn Ala Leu  Leu Gln Asn
    2045                2050                2055

Gln Ala  Ala Glu Leu Ile Leu  Thr Asn Leu Ser Ile  Gln Asp Lys
    2060                2065                2070

Thr Ile  Glu Glu Leu Asp Ala  Glu Lys Thr Val Leu  Glu Lys Ser
    2075                2080                2085

Lys Ala  Gly Ala Gln Ser Arg  Phe Asp Ser Tyr Gly  Lys Leu Tyr
    2090                2095                2100

Asp Glu  Asn Ile Asn Ala Gly  Glu Asn Gln Ala Met  Thr Leu Arg
    2105                2110                2115

Ala Ser  Ala Ala Gly Leu Thr  Thr Ala Val Gln Ala  Ser Arg Leu
    2120                2125                2130

Ala Gly  Ala Ala Ala Asp Leu  Val Pro Asn Ile Phe  Gly Phe Ala
    2135                2140                2145

Gly Gly  Gly Ser Arg Trp Gly  Ala Ile Ala Glu Ala  Thr Gly Tyr
    2150                2155                2160

Val Met  Glu Phe Ser Ala Asn  Val Met Asn Thr Glu  Ala Asp Lys
    2165                2170                2175

Ile Ser  Gln Ser Glu Thr Tyr  Arg Arg Arg Arg Gln  Glu Trp Glu
    2180                2185                2190

Ile Gln  Arg Asn Asn Ala Glu  Ala Glu Leu Lys Gln  Ile Asp Ala
    2195                2200                2205

Gln Leu  Lys Ser Leu Ala Val  Arg Arg Glu Ala Ala  Val Leu Gln
    2210                2215                2220

Lys Thr  Ser Leu Lys Thr Gln  Gln Glu Gln Thr Gln  Ser Gln Leu
    2225                2230                2235

Ala Phe  Leu Gln Arg Lys Phe  Ser Asn Gln Ala Leu  Tyr Asn Trp
    2240                2245                2250

Leu Arg  Gly Arg Leu Ala Ala  Ile Tyr Phe Gln Phe  Tyr Asp Leu
    2255                2260                2265

Ala Val  Ala Arg Cys Leu Met  Ala Glu Gln Ala Tyr  Arg Trp Glu
    2270                2275                2280

Leu Asn  Asp Asp Ser Ala Arg  Phe Ile Lys Pro Gly  Ala Trp Gln
    2285                2290                2295

Gly Thr  Tyr Ala Gly Leu Leu  Ala Gly Glu Thr Leu  Met Leu Ser
    2300                2305                2310

Leu Ala  Gln Met Glu Asp Ala  His Leu Lys Arg Asp  Lys Arg Ala
    2315                2320                2325

Leu Glu  Val Glu Arg Thr Val  Ser Leu Ala Glu Val  Tyr Ala Gly
    2330                2335                2340

Leu Pro  Lys Asp Asn Gly Pro  Phe Ser Leu Ala Gln  Glu Ile Asp
    2345                2350                2355

Lys Leu  Val Ser Gln Gly Ser  Gly Ser Ala Gly Ser  Gly Asn Asn
    2360                2365                2370

Asn Leu  Ala Phe Gly Ala Gly  Thr Asp Thr Lys Thr  Ser Leu Gln
    2375                2380                2385

Ala Ser  Val Ser Phe Ala Asp  Leu Lys Ile Arg Glu  Asp Tyr Pro
    2390                2395                2400
```

-continued

```
Ala Ser  Leu Gly Lys Ile Arg  Arg Ile Lys Gln Ile  Ser Val Thr
    2405                2410                2415

Leu Pro  Ala Leu Leu Gly Pro  Tyr Gln Asp Val Gln  Ala Ile Leu
    2420                2425                2430

Ser Tyr  Gly Asp Lys Ala Gly  Leu Ala Asn Gly Cys  Glu Ala Leu
    2435                2440                2445

Ala Val  Ser His Gly Met Asn  Asp Ser Gly Gln Phe  Gln Leu Asp
    2450                2455                2460

Phe Asn  Asp Gly Lys Phe Leu  Pro Phe Glu Gly Ile  Ala Ile Asp
    2465                2470                2475

Gln Gly  Thr Leu Thr Leu Ser  Phe Pro Asn Ala Ser  Met Pro Glu
    2480                2485                2490

Lys Gly  Lys Gln Ala Thr Met  Leu Lys Thr Leu Asn  Asp Ile Ile
    2495                2500                2505

Leu His  Ile Arg Tyr Thr Ile  Lys
    2510                2515


<210> SEQ ID NO 3
<211> LENGTH: 4431
<212> TYPE: DNA
<213> ORGANISM: Photorhabdus luminescens
<220> FEATURE:
<221> NAME/KEY: CDS
<222> LOCATION: (1)..(4431)

<400> SEQUENCE: 3

atg cag aat tca caa aca ttc agt gtt acc gag ctg tca tta ccc aaa       48
Met Gln Asn Ser Gln Thr Phe Ser Val Thr Glu Leu Ser Leu Pro Lys
1               5                   10                  15

ggc ggc ggc gct att acc ggt atg ggt gaa gca tta aca cca gcc ggg       96
Gly Gly Gly Ala Ile Thr Gly Met Gly Glu Ala Leu Thr Pro Ala Gly
            20                  25                  30

ccg gat ggt atg gcc gcc tta tcc ctg cca tta ccc att tcc gcc ggg      144
Pro Asp Gly Met Ala Ala Leu Ser Leu Pro Leu Pro Ile Ser Ala Gly
        35                  40                  45

cgt ggt tac gca ccc tcg ctc act ctg aat tac aac agt gga acc ggt      192
Arg Gly Tyr Ala Pro Ser Leu Thr Leu Asn Tyr Asn Ser Gly Thr Gly
    50                  55                  60

aac agc cca ttt ggt ctc ggt tgg gac tgc ggc gtc atg gca att cgt      240
Asn Ser Pro Phe Gly Leu Gly Trp Asp Cys Gly Val Met Ala Ile Arg
65                  70                  75                  80

cgt cgc acc agt acc ggc gta ccg aat tac gat gaa acc gat act ttt      288
Arg Arg Thr Ser Thr Gly Val Pro Asn Tyr Asp Glu Thr Asp Thr Phe
                85                  90                  95

ctg ggg ccg gaa ggt gaa gtg ttg gtc gta gca tta aat gag gca ggt      336
Leu Gly Pro Glu Gly Glu Val Leu Val Val Ala Leu Asn Glu Ala Gly
            100                 105                 110

caa gct gat atc cgc agt gaa tcc tca ttg cag ggc atc aat ttg ggt      384
Gln Ala Asp Ile Arg Ser Glu Ser Ser Leu Gln Gly Ile Asn Leu Gly
        115                 120                 125

gcg acc ttc acc gtt acc tgt tat cgc tcc cgc cta gaa agc cac ttt      432
Ala Thr Phe Thr Val Thr Cys Tyr Arg Ser Arg Leu Glu Ser His Phe
    130                 135                 140

aac cgg ttg gaa tac tgg caa ccc caa aca acc ggc gca acc gat ttc      480
Asn Arg Leu Glu Tyr Trp Gln Pro Gln Thr Thr Gly Ala Thr Asp Phe
145                 150                 155                 160

tgg ctg ata tac agc ccc gac gga cag gtc cat tta ctg ggc aaa aat      528
Trp Leu Ile Tyr Ser Pro Asp Gly Gln Val His Leu Leu Gly Lys Asn
                165                 170                 175
```

-continued

```
cct cag gca cgt atc agc aat cca ctc aat gtt aac caa aca gcg caa       576
Pro Gln Ala Arg Ile Ser Asn Pro Leu Asn Val Asn Gln Thr Ala Gln
            180                 185                 190

tgg ctg ttg gaa gcc tcg ata tca tcc cac agc gaa cag att tat tat       624
Trp Leu Leu Glu Ala Ser Ile Ser Ser His Ser Glu Gln Ile Tyr Tyr
        195                 200                 205

caa tat cgc gct gaa gat gaa gca ggt tgt gaa acc gac gag cta gca       672
Gln Tyr Arg Ala Glu Asp Glu Ala Gly Cys Glu Thr Asp Glu Leu Ala
    210                 215                 220

gcc cac ccc agc gca acc gtt cag cgc tac ctg caa aca gta cat tac       720
Ala His Pro Ser Ala Thr Val Gln Arg Tyr Leu Gln Thr Val His Tyr
225                 230                 235                 240

ggg aac ctg acc gcc agc gac gtt ttt cct aca cta aac gga gat gac       768
Gly Asn Leu Thr Ala Ser Asp Val Phe Pro Thr Leu Asn Gly Asp Asp
                245                 250                 255

cca ctt aaa tct ggc tgg atg ttc tgt tta gta ttt gac tac ggt gag       816
Pro Leu Lys Ser Gly Trp Met Phe Cys Leu Val Phe Asp Tyr Gly Glu
            260                 265                 270

cgc aaa aac agc tta tct gaa atg ccg ctg ttt aaa gcc aca ggc aat       864
Arg Lys Asn Ser Leu Ser Glu Met Pro Leu Phe Lys Ala Thr Gly Asn
        275                 280                 285

tgg ctt tgc cga aaa gac cgt ttt tcc cgt tat gag tac ggt ttt gaa       912
Trp Leu Cys Arg Lys Asp Arg Phe Ser Arg Tyr Glu Tyr Gly Phe Glu
    290                 295                 300

ttg cgt act cgc cgc tta tgc cgc caa ata ctg atg ttt cac cgt cta       960
Leu Arg Thr Arg Arg Leu Cys Arg Gln Ile Leu Met Phe His Arg Leu
305                 310                 315                 320

caa acc cta tct ggt cag gca aag ggg gat gat gaa cct gcg cta gtg      1008
Gln Thr Leu Ser Gly Gln Ala Lys Gly Asp Asp Glu Pro Ala Leu Val
                325                 330                 335

tcg cgt ctg ata ctg gat tat gac gaa aac gcg atg gtc agt acg ctc      1056
Ser Arg Leu Ile Leu Asp Tyr Asp Glu Asn Ala Met Val Ser Thr Leu
            340                 345                 350

gtt tct gtc cgc cgg gta ggc cat gag gac aac aac acg gtt acc gcg      1104
Val Ser Val Arg Arg Val Gly His Glu Asp Asn Asn Thr Val Thr Ala
        355                 360                 365

ctg cca cca ctg gaa ctg gcc tat cag cct ttt gag cca gaa caa acc      1152
Leu Pro Pro Leu Glu Leu Ala Tyr Gln Pro Phe Glu Pro Glu Gln Thr
    370                 375                 380

gca ctc tgg caa tca atg gat gta ctg gca aat ttc aac acc att cag      1200
Ala Leu Trp Gln Ser Met Asp Val Leu Ala Asn Phe Asn Thr Ile Gln
385                 390                 395                 400

cgc tgg caa ctg ctt gac ctg aaa gga gaa ggc gtg ccc ggc att ctc      1248
Arg Trp Gln Leu Leu Asp Leu Lys Gly Glu Gly Val Pro Gly Ile Leu
                405                 410                 415

tat cag gat aga aat ggc tgg tgg tat cga tct gcc caa cgt cag gcc      1296
Tyr Gln Asp Arg Asn Gly Trp Trp Tyr Arg Ser Ala Gln Arg Gln Ala
            420                 425                 430

ggg gaa gag atg aat gcg gtc acc tgg ggg aaa atg caa ctc ctt ccc      1344
Gly Glu Glu Met Asn Ala Val Thr Trp Gly Lys Met Gln Leu Leu Pro
        435                 440                 445

atc aca cca gct gtg cag gat aac gcc tca ctg atg gat att aac ggt      1392
Ile Thr Pro Ala Val Gln Asp Asn Ala Ser Leu Met Asp Ile Asn Gly
    450                 455                 460

gac ggg caa ctg gac tgg gtg att acc ggg ccg ggg cta agg ggc tat      1440
Asp Gly Gln Leu Asp Trp Val Ile Thr Gly Pro Gly Leu Arg Gly Tyr
465                 470                 475                 480

cac agc caa cac ccg gat ggc agt tgg acg cgt ttt acg cca tta cat      1488
His Ser Gln His Pro Asp Gly Ser Trp Thr Arg Phe Thr Pro Leu His
```

-continued

```
                485                 490                 495

gcc ctg ccg ata gaa tat tct cat cct cgc gct caa ctt gcc gat tta     1536
Ala Leu Pro Ile Glu Tyr Ser His Pro Arg Ala Gln Leu Ala Asp Leu
            500                 505                 510

atg gga gcc ggg ctg tcc gat tta gtg cta att ggt ccc aaa agt gtg     1584
Met Gly Ala Gly Leu Ser Asp Leu Val Leu Ile Gly Pro Lys Ser Val
        515                 520                 525

cgc tta tat gtc aat aac cgt gat ggt ttt acc gaa ggg cgg gat gtg     1632
Arg Leu Tyr Val Asn Asn Arg Asp Gly Phe Thr Glu Gly Arg Asp Val
    530                 535                 540

gtg caa tcc ggt gat atc acc ctg ccg cta ccg ggc gcc gat gcc cgt     1680
Val Gln Ser Gly Asp Ile Thr Leu Pro Leu Pro Gly Ala Asp Ala Arg
545                 550                 555                 560

aag tta gtg gca ttt agt gac gta ctg ggt tca ggc caa gca cat ctg     1728
Lys Leu Val Ala Phe Ser Asp Val Leu Gly Ser Gly Gln Ala His Leu
                565                 570                 575

gtt gaa gtt agt gca act caa gtc acc tgc tgg ccg aat ctg ggg cat     1776
Val Glu Val Ser Ala Thr Gln Val Thr Cys Trp Pro Asn Leu Gly His
            580                 585                 590

ggc cgt ttt ggt cag cca atc gta ttg ccg gga ttc agc caa tct gcc     1824
Gly Arg Phe Gly Gln Pro Ile Val Leu Pro Gly Phe Ser Gln Ser Ala
        595                 600                 605

gcc agt ttt aat cct gat cga gtt cat ctg gcc gat ttg gat ggg agc     1872
Ala Ser Phe Asn Pro Asp Arg Val His Leu Ala Asp Leu Asp Gly Ser
    610                 615                 620

ggc cct gcc gat ttg att tat gtt cat gct gac cgt ctg gat att ttc     1920
Gly Pro Ala Asp Leu Ile Tyr Val His Ala Asp Arg Leu Asp Ile Phe
625                 630                 635                 640

agc aat gaa agt ggc aac ggt ttt gca aaa cca ttc aca ctc tct ttt     1968
Ser Asn Glu Ser Gly Asn Gly Phe Ala Lys Pro Phe Thr Leu Ser Phe
                645                 650                 655

cct gac ggc ctg cgt ttt gat gat acc tgc cag ttg caa gta gcc gat     2016
Pro Asp Gly Leu Arg Phe Asp Asp Thr Cys Gln Leu Gln Val Ala Asp
            660                 665                 670

gta caa ggg tta ggc gtt gtc agc ctg atc cta agc gta ccg cat atg     2064
Val Gln Gly Leu Gly Val Val Ser Leu Ile Leu Ser Val Pro His Met
        675                 680                 685

gcg cca cat cat tgg cgc tgc gat ctg acc aac gcg aaa ccg tgg tta     2112
Ala Pro His His Trp Arg Cys Asp Leu Thr Asn Ala Lys Pro Trp Leu
    690                 695                 700

ctc agt gaa acg aac aac aat atg ggg gcc aat cac acc ttg cat tac     2160
Leu Ser Glu Thr Asn Asn Asn Met Gly Ala Asn His Thr Leu His Tyr
705                 710                 715                 720

cgt agc tct gtc cag ttc tgg ctg gat gaa aaa gct gcg gca ttg gct     2208
Arg Ser Ser Val Gln Phe Trp Leu Asp Glu Lys Ala Ala Ala Leu Ala
                725                 730                 735

acc gga caa aca ccg gtc tgt tac ctg ccc ttc ccg gtc cat acc ctt     2256
Thr Gly Gln Thr Pro Val Cys Tyr Leu Pro Phe Pro Val His Thr Leu
            740                 745                 750

tgg caa aca gaa acc gag gat gaa atc agc ggc aat aag tta gtg acc     2304
Trp Gln Thr Glu Thr Glu Asp Glu Ile Ser Gly Asn Lys Leu Val Thr
        755                 760                 765

acg tta cgt tat gct cac ggc gct tgg gat gga cgt gaa cgg gaa ttt     2352
Thr Leu Arg Tyr Ala His Gly Ala Trp Asp Gly Arg Glu Arg Glu Phe
    770                 775                 780

cgt ggc ttt ggt tat gtt gag cag aca gac agc cat caa ctc gct caa     2400
Arg Gly Phe Gly Tyr Val Glu Gln Thr Asp Ser His Gln Leu Ala Gln
785                 790                 795                 800

ggc aat gcg ccg gaa cgt aca cca ccg gca ctc acc aaa agc tgg tat     2448
```

-continued

```
Gly Asn Ala Pro Glu Arg Thr Pro Pro Ala Leu Thr Lys Ser Trp Tyr
                805                 810                 815

gcc acc gga tta cct gcg gta gat aat gcg tta tcc gcc ggg tat tgg     2496
Ala Thr Gly Leu Pro Ala Val Asp Asn Ala Leu Ser Ala Gly Tyr Trp
            820                 825                 830

cgt ggc gat aag caa gct ttc gcc ggt ttt acg cca cgt ttt act ctc     2544
Arg Gly Asp Lys Gln Ala Phe Ala Gly Phe Thr Pro Arg Phe Thr Leu
        835                 840                 845

tgg aaa gag ggc aaa gat gtt cca ctg aca ccg gaa gat gac cat aat     2592
Trp Lys Glu Gly Lys Asp Val Pro Leu Thr Pro Glu Asp Asp His Asn
    850                 855                 860

cta tac tgg tta aac cgg gcg cta aaa ggt cag cca ctg cgt agt gaa     2640
Leu Tyr Trp Leu Asn Arg Ala Leu Lys Gly Gln Pro Leu Arg Ser Glu
865                 870                 875                 880

ctc tac ggg ctg gat ggc agc gca cag caa cag atc ccc tat aca gtg     2688
Leu Tyr Gly Leu Asp Gly Ser Ala Gln Gln Gln Ile Pro Tyr Thr Val
                885                 890                 895

act gaa tcc cgt cca cag gtg cgc caa tta caa gat ggc gcc acc gtt     2736
Thr Glu Ser Arg Pro Gln Val Arg Gln Leu Gln Asp Gly Ala Thr Val
            900                 905                 910

tcc ccg gtg ctc tgg gcc tca gtc gtg gaa agc cgt agt tat cac tac     2784
Ser Pro Val Leu Trp Ala Ser Val Val Glu Ser Arg Ser Tyr His Tyr
        915                 920                 925

gaa cgt att atc agt gat ccc cag tgc aat cag gat atc acg ttg tcc     2832
Glu Arg Ile Ile Ser Asp Pro Gln Cys Asn Gln Asp Ile Thr Leu Ser
    930                 935                 940

agt gac cta ttc ggg caa cca ctg aaa cag gtt tcc gta caa tat ccc     2880
Ser Asp Leu Phe Gly Gln Pro Leu Lys Gln Val Ser Val Gln Tyr Pro
945                 950                 955                 960

cgc cgc aac aaa cca aca acc aat ccg tat ccc gat acc cta ccg gat     2928
Arg Arg Asn Lys Pro Thr Thr Asn Pro Tyr Pro Asp Thr Leu Pro Asp
                965                 970                 975

acg ctg ttt gcc agc agt tat gac gat caa caa cag cta ttg cga tta     2976
Thr Leu Phe Ala Ser Ser Tyr Asp Asp Gln Gln Gln Leu Leu Arg Leu
            980                 985                 990

acc tgc cga caa tcc agt tgg cac  cat ctt att ggt aat  gag cta aga   3024
Thr Cys Arg Gln Ser Ser Trp His  His Leu Ile Gly Asn  Glu Leu Arg
        995                 1000                1005

gtg ttg  gga tta ccg gat ggc  aca cgc agt gat gcc  ttt act tac     3069
Val Leu  Gly Leu Pro Asp Gly  Thr Arg Ser Asp Ala  Phe Thr Tyr
    1010                1015                1020

gat gcc  aaa cag gta cct gtc  gat ggc tta aat ctg  gaa acc ctg     3114
Asp Ala  Lys Gln Val Pro Val  Asp Gly Leu Asn Leu  Glu Thr Leu
    1025                1030                1035

tgt gct  gaa aat agc ctg att  gcc gat gat aaa cct  cgc gaa tac     3159
Cys Ala  Glu Asn Ser Leu Ile  Ala Asp Asp Lys Pro  Arg Glu Tyr
    1040                1045                1050

ctc aat  cag caa cga acg ttc  tat acc gac ggg aaa  aac caa aca     3204
Leu Asn  Gln Gln Arg Thr Phe  Tyr Thr Asp Gly Lys  Asn Gln Thr
    1055                1060                1065

ccg ctg  aaa aca ccg aca cga  caa gcg tta atc gcc  ttt acc gaa     3249
Pro Leu  Lys Thr Pro Thr Arg  Gln Ala Leu Ile Ala  Phe Thr Glu
    1070                1075                1080

acg gcg  gta tta acg gaa tct  ctg tta tcc gcg ttt  gat ggc ggt     3294
Thr Ala  Val Leu Thr Glu Ser  Leu Leu Ser Ala Phe  Asp Gly Gly
    1085                1090                1095

att acg  cca gac gaa tta ccg  gga ata ctg aca cag  gcc gga tac     3339
Ile Thr  Pro Asp Glu Leu Pro  Gly Ile Leu Thr Gln  Ala Gly Tyr
    1100                1105                1110
```

-continued

```
caa caa  gag cct tat ctg ttt  cca cgc acc ggc gaa  aac aaa gtt      3384
Gln Gln  Glu Pro Tyr Leu Phe  Pro Arg Thr Gly Glu  Asn Lys Val
    1115                 1120                 1125

tgg gta  gcg cgt caa ggc tat  acc gat tac ggg acg  gaa gca caa      3429
Trp Val  Ala Arg Gln Gly Tyr  Thr Asp Tyr Gly Thr  Glu Ala Gln
    1130                 1135                 1140

ttt tgg  cgt cct gtc gca caa  cgt aac agc ctg tta  acc ggg aaa      3474
Phe Trp  Arg Pro Val Ala Gln  Arg Asn Ser Leu Leu  Thr Gly Lys
    1145                 1150                 1155

atg acg  tta aaa tgg gat act  cac tat tgt gtc atc  acc caa acc      3519
Met Thr  Leu Lys Trp Asp Thr  His Tyr Cys Val Ile  Thr Gln Thr
    1160                 1165                 1170

caa gat  gct gcc ggc ctc acc  gtc tca gcc aat tat  gac tgg cgt      3564
Gln Asp  Ala Ala Gly Leu Thr  Val Ser Ala Asn Tyr  Asp Trp Arg
    1175                 1180                 1185

ttt ctc  aca cca acg caa ctg  act gac atc aac gat  aat gtg cat      3609
Phe Leu  Thr Pro Thr Gln Leu  Thr Asp Ile Asn Asp  Asn Val His
    1190                 1195                 1200

ctc atc  acc ttg gat gct ctg  gga cgc cct gtc acg  caa cgt ttc      3654
Leu Ile  Thr Leu Asp Ala Leu  Gly Arg Pro Val Thr  Gln Arg Phe
    1205                 1210                 1215

tgg ggg  atc gaa agc ggt gtg  gca aca ggt tac tct  tca tca gaa      3699
Trp Gly  Ile Glu Ser Gly Val  Ala Thr Gly Tyr Ser  Ser Ser Glu
    1220                 1225                 1230

gaa aaa  cca ttc tct cca cca  aac gat atc gat acc  gct att aat      3744
Glu Lys  Pro Phe Ser Pro Pro  Asn Asp Ile Asp Thr  Ala Ile Asn
    1235                 1240                 1245

cta acc  gga cca ctc cct gtc  gca cag tgt ctg gtc  tat gca ccg      3789
Leu Thr  Gly Pro Leu Pro Val  Ala Gln Cys Leu Val  Tyr Ala Pro
    1250                 1255                 1260

gac agt  tgg atg cca cta ttc  agt caa gaa acc ttc  aac aca tta      3834
Asp Ser  Trp Met Pro Leu Phe  Ser Gln Glu Thr Phe  Asn Thr Leu
    1265                 1270                 1275

acg cag  gaa gag cag gag acg  ctg cgt gat tca cgt  att atc acg      3879
Thr Gln  Glu Glu Gln Glu Thr  Leu Arg Asp Ser Arg  Ile Ile Thr
    1280                 1285                 1290

gaa gat  tgg cgt att tgc gca  ctg act cgc cgc cgt  tgg cta caa      3924
Glu Asp  Trp Arg Ile Cys Ala  Leu Thr Arg Arg Arg  Trp Leu Gln
    1295                 1300                 1305

agt caa  aag atc agt aca cca  tta gtt aaa ctg tta  acc aac agc      3969
Ser Gln  Lys Ile Ser Thr Pro  Leu Val Lys Leu Leu  Thr Asn Ser
    1310                 1315                 1320

att ggt  tta cct ccc cat aac  ctt acg ctg acc aca  gac cgt tat      4014
Ile Gly  Leu Pro Pro His Asn  Leu Thr Leu Thr Thr  Asp Arg Tyr
    1325                 1330                 1335

gac cgc  gac tct gag cag caa  att cgc caa caa gtc  gca ttt agt      4059
Asp Arg  Asp Ser Glu Gln Gln  Ile Arg Gln Gln Val  Ala Phe Ser
    1340                 1345                 1350

gat ggt  ttt ggc cgt ctg cta  caa gcg tct gta cga  cat gag gca      4104
Asp Gly  Phe Gly Arg Leu Leu  Gln Ala Ser Val Arg  His Glu Ala
    1355                 1360                 1365

ggc gaa  gcc tgg caa cgt aac  caa gac ggt tct ctg  gtg aca aaa      4149
Gly Glu  Ala Trp Gln Arg Asn  Gln Asp Gly Ser Leu  Val Thr Lys
    1370                 1375                 1380

gtg gag  aat acc aaa acg cgt  tgg gcg gtc acg gga  cgc acc gaa      4194
Val Glu  Asn Thr Lys Thr Arg  Trp Ala Val Thr Gly  Arg Thr Glu
    1385                 1390                 1395

tat gat  aat aaa ggg caa acg  ata cgc act tat cag  ccc tat ttc      4239
Tyr Asp  Asn Lys Gly Gln Thr  Ile Arg Thr Tyr Gln  Pro Tyr Phe
    1400                 1405                 1410
```

-continued

```
ctc aac  gac tgg cga tat gtc  agt gat gac agc gcc  aga aaa gaa      4284
Leu Asn  Asp Trp Arg Tyr Val  Ser Asp Asp Ser Ala  Arg Lys Glu
    1415                1420                1425

gcc tat  gcg gat act cat att  tat gat cca att ggg  cga gaa atc      4329
Ala Tyr  Ala Asp Thr His Ile  Tyr Asp Pro Ile Gly  Arg Glu Ile
    1430                1435                1440

cgg gtt  att act gca aaa ggc  tgg ctg cgc caa agc  caa tat ttc      4374
Arg Val  Ile Thr Ala Lys Gly  Trp Leu Arg Gln Ser  Gln Tyr Phe
    1445                1450                1455

ccg tgg  ttt acc gtg agt gag  gat gag aat gat acg  gcc gct gat      4419
Pro Trp  Phe Thr Val Ser Glu  Asp Glu Asn Asp Thr  Ala Ala Asp
    1460                1465                1470

gcg ctg  gtg taa                                                   4431
Ala Leu  Val
    1475


<210> SEQ ID NO 4
<211> LENGTH: 1476
<212> TYPE: PRT
<213> ORGANISM: Photorhabdus luminescens

<400> SEQUENCE: 4

Met Gln Asn Ser Gln Thr Phe Ser Val Thr Glu Leu Ser Leu Pro Lys
1               5                   10                  15

Gly Gly Gly Ala Ile Thr Gly Met Gly Glu Ala Leu Thr Pro Ala Gly
            20                  25                  30

Pro Asp Gly Met Ala Ala Leu Ser Leu Pro Leu Pro Ile Ser Ala Gly
        35                  40                  45

Arg Gly Tyr Ala Pro Ser Leu Thr Leu Asn Tyr Asn Ser Gly Thr Gly
    50                  55                  60

Asn Ser Pro Phe Gly Leu Gly Trp Asp Cys Gly Val Met Ala Ile Arg
65                  70                  75                  80

Arg Arg Thr Ser Thr Gly Val Pro Asn Tyr Asp Glu Thr Asp Thr Phe
                85                  90                  95

Leu Gly Pro Glu Gly Glu Val Leu Val Val Ala Leu Asn Glu Ala Gly
            100                 105                 110

Gln Ala Asp Ile Arg Ser Glu Ser Ser Leu Gln Gly Ile Asn Leu Gly
        115                 120                 125

Ala Thr Phe Thr Val Thr Cys Tyr Arg Ser Arg Leu Glu Ser His Phe
    130                 135                 140

Asn Arg Leu Glu Tyr Trp Gln Pro Gln Thr Thr Gly Ala Thr Asp Phe
145                 150                 155                 160

Trp Leu Ile Tyr Ser Pro Asp Gly Gln Val His Leu Leu Gly Lys Asn
                165                 170                 175

Pro Gln Ala Arg Ile Ser Asn Pro Leu Asn Val Asn Gln Thr Ala Gln
            180                 185                 190

Trp Leu Leu Glu Ala Ser Ile Ser Ser His Ser Glu Gln Ile Tyr Tyr
        195                 200                 205

Gln Tyr Arg Ala Glu Asp Glu Ala Gly Cys Glu Thr Asp Glu Leu Ala
    210                 215                 220

Ala His Pro Ser Ala Thr Val Gln Arg Tyr Leu Gln Thr Val His Tyr
225                 230                 235                 240

Gly Asn Leu Thr Ala Ser Asp Val Phe Pro Thr Leu Asn Gly Asp Asp
                245                 250                 255

Pro Leu Lys Ser Gly Trp Met Phe Cys Leu Val Phe Asp Tyr Gly Glu
            260                 265                 270
```

-continued

```
Arg Lys Asn Ser Leu Ser Glu Met Pro Leu Phe Lys Ala Thr Gly Asn
        275                 280                 285

Trp Leu Cys Arg Lys Asp Arg Phe Ser Arg Tyr Glu Tyr Gly Phe Glu
    290                 295                 300

Leu Arg Thr Arg Arg Leu Cys Arg Gln Ile Leu Met Phe His Arg Leu
305                 310                 315                 320

Gln Thr Leu Ser Gly Gln Ala Lys Gly Asp Asp Glu Pro Ala Leu Val
                325                 330                 335

Ser Arg Leu Ile Leu Asp Tyr Asp Glu Asn Ala Met Val Ser Thr Leu
            340                 345                 350

Val Ser Val Arg Arg Val Gly His Glu Asp Asn Asn Thr Val Thr Ala
        355                 360                 365

Leu Pro Pro Leu Glu Leu Ala Tyr Gln Pro Phe Glu Pro Glu Gln Thr
    370                 375                 380

Ala Leu Trp Gln Ser Met Asp Val Leu Ala Asn Phe Asn Thr Ile Gln
385                 390                 395                 400

Arg Trp Gln Leu Leu Asp Leu Lys Gly Glu Gly Val Pro Gly Ile Leu
                405                 410                 415

Tyr Gln Asp Arg Asn Gly Trp Trp Tyr Arg Ser Ala Gln Arg Gln Ala
            420                 425                 430

Gly Glu Glu Met Asn Ala Val Thr Trp Gly Lys Met Gln Leu Leu Pro
        435                 440                 445

Ile Thr Pro Ala Val Gln Asp Asn Ala Ser Leu Met Asp Ile Asn Gly
    450                 455                 460

Asp Gly Gln Leu Asp Trp Val Ile Thr Gly Pro Gly Leu Arg Gly Tyr
465                 470                 475                 480

His Ser Gln His Pro Asp Gly Ser Trp Thr Arg Phe Thr Pro Leu His
                485                 490                 495

Ala Leu Pro Ile Glu Tyr Ser His Pro Arg Ala Gln Leu Ala Asp Leu
            500                 505                 510

Met Gly Ala Gly Leu Ser Asp Leu Val Leu Ile Gly Pro Lys Ser Val
        515                 520                 525

Arg Leu Tyr Val Asn Asn Arg Asp Gly Phe Thr Glu Gly Arg Asp Val
    530                 535                 540

Val Gln Ser Gly Asp Ile Thr Leu Pro Leu Pro Gly Ala Asp Ala Arg
545                 550                 555                 560

Lys Leu Val Ala Phe Ser Asp Val Leu Gly Ser Gly Gln Ala His Leu
                565                 570                 575

Val Glu Val Ser Ala Thr Gln Val Thr Cys Trp Pro Asn Leu Gly His
            580                 585                 590

Gly Arg Phe Gly Gln Pro Ile Val Leu Pro Gly Phe Ser Gln Ser Ala
        595                 600                 605

Ala Ser Phe Asn Pro Asp Arg Val His Leu Ala Asp Leu Asp Gly Ser
    610                 615                 620

Gly Pro Ala Asp Leu Ile Tyr Val His Ala Asp Arg Leu Asp Ile Phe
625                 630                 635                 640

Ser Asn Glu Ser Gly Asn Gly Phe Ala Lys Pro Phe Thr Leu Ser Phe
                645                 650                 655

Pro Asp Gly Leu Arg Phe Asp Asp Thr Cys Gln Leu Gln Val Ala Asp
            660                 665                 670

Val Gln Gly Leu Gly Val Val Ser Leu Ile Leu Ser Val Pro His Met
        675                 680                 685
```

-continued

```
Ala Pro His His Trp Arg Cys Asp Leu Thr Asn Ala Lys Pro Trp Leu
    690                 695                 700

Leu Ser Glu Thr Asn Asn Asn Met Gly Ala Asn His Thr Leu His Tyr
705                 710                 715                 720

Arg Ser Ser Val Gln Phe Trp Leu Asp Glu Lys Ala Ala Ala Leu Ala
                725                 730                 735

Thr Gly Gln Thr Pro Val Cys Tyr Leu Pro Phe Pro Val His Thr Leu
            740                 745                 750

Trp Gln Thr Glu Thr Glu Asp Glu Ile Ser Gly Asn Lys Leu Val Thr
        755                 760                 765

Thr Leu Arg Tyr Ala His Gly Ala Trp Asp Gly Arg Glu Arg Glu Phe
    770                 775                 780

Arg Gly Phe Gly Tyr Val Glu Gln Thr Asp Ser His Gln Leu Ala Gln
785                 790                 795                 800

Gly Asn Ala Pro Glu Arg Thr Pro Pro Ala Leu Thr Lys Ser Trp Tyr
                805                 810                 815

Ala Thr Gly Leu Pro Ala Val Asp Asn Ala Leu Ser Ala Gly Tyr Trp
            820                 825                 830

Arg Gly Asp Lys Gln Ala Phe Ala Gly Phe Thr Pro Arg Phe Thr Leu
        835                 840                 845

Trp Lys Glu Gly Lys Asp Val Pro Leu Thr Pro Glu Asp Asp His Asn
    850                 855                 860

Leu Tyr Trp Leu Asn Arg Ala Leu Lys Gly Gln Pro Leu Arg Ser Glu
865                 870                 875                 880

Leu Tyr Gly Leu Asp Gly Ser Ala Gln Gln Gln Ile Pro Tyr Thr Val
                885                 890                 895

Thr Glu Ser Arg Pro Gln Val Arg Gln Leu Gln Asp Gly Ala Thr Val
            900                 905                 910

Ser Pro Val Leu Trp Ala Ser Val Val Glu Ser Arg Ser Tyr His Tyr
        915                 920                 925

Glu Arg Ile Ile Ser Asp Pro Gln Cys Asn Gln Asp Ile Thr Leu Ser
    930                 935                 940

Ser Asp Leu Phe Gly Gln Pro Leu Lys Gln Val Ser Val Gln Tyr Pro
945                 950                 955                 960

Arg Arg Asn Lys Pro Thr Thr Asn Pro Tyr Pro Asp Thr Leu Pro Asp
                965                 970                 975

Thr Leu Phe Ala Ser Ser Tyr Asp Asp Gln Gln Gln Leu Leu Arg Leu
            980                 985                 990

Thr Cys Arg Gln Ser Ser Trp His  His Leu Ile Gly Asn  Glu Leu Arg
        995                 1000                1005

Val Leu  Gly Leu Pro Asp Gly  Thr Arg Ser Asp Ala  Phe Thr Tyr
    1010                1015                1020

Asp Ala  Lys Gln Val Pro Val  Asp Gly Leu Asn Leu  Glu Thr Leu
    1025                1030                1035

Cys Ala  Glu Asn Ser Leu Ile  Ala Asp Asp Lys Pro  Arg Glu Tyr
    1040                1045                1050

Leu Asn  Gln Gln Arg Thr Phe  Tyr Thr Asp Gly Lys  Asn Gln Thr
    1055                1060                1065

Pro Leu  Lys Thr Pro Thr Arg  Gln Ala Leu Ile Ala  Phe Thr Glu
    1070                1075                1080

Thr Ala  Val Leu Thr Glu Ser  Leu Leu Ser Ala Phe  Asp Gly Gly
    1085                1090                1095

Ile Thr  Pro Asp Glu Leu Pro  Gly Ile Leu Thr Gln  Ala Gly Tyr
```

-continued

```
    1100                1105                1110

Gln Gln  Glu Pro Tyr Leu Phe  Pro Arg Thr Gly Glu  Asn Lys Val
    1115                1120                1125

Trp Val  Ala Arg Gln Gly Tyr  Thr Asp Tyr Gly Thr  Glu Ala Gln
    1130                1135                1140

Phe Trp  Arg Pro Val Ala Gln  Arg Asn Ser Leu Leu  Thr Gly Lys
    1145                1150                1155

Met Thr  Leu Lys Trp Asp Thr  His Tyr Cys Val Ile  Thr Gln Thr
    1160                1165                1170

Gln Asp  Ala Ala Gly Leu Thr  Val Ser Ala Asn Tyr  Asp Trp Arg
    1175                1180                1185

Phe Leu  Thr Pro Thr Gln Leu  Thr Asp Ile Asn Asp  Asn Val His
    1190                1195                1200

Leu Ile  Thr Leu Asp Ala Leu  Gly Arg Pro Val Thr  Gln Arg Phe
    1205                1210                1215

Trp Gly  Ile Glu Ser Gly Val  Ala Thr Gly Tyr Ser  Ser Ser Glu
    1220                1225                1230

Glu Lys  Pro Phe Ser Pro Pro  Asn Asp Ile Asp Thr  Ala Ile Asn
    1235                1240                1245

Leu Thr  Gly Pro Leu Pro Val  Ala Gln Cys Leu Val  Tyr Ala Pro
    1250                1255                1260

Asp Ser  Trp Met Pro Leu Phe  Ser Gln Glu Thr Phe  Asn Thr Leu
    1265                1270                1275

Thr Gln  Glu Glu Gln Glu Thr  Leu Arg Asp Ser Arg  Ile Ile Thr
    1280                1285                1290

Glu Asp  Trp Arg Ile Cys Ala  Leu Thr Arg Arg Arg  Trp Leu Gln
    1295                1300                1305

Ser Gln  Lys Ile Ser Thr Pro  Leu Val Lys Leu Leu  Thr Asn Ser
    1310                1315                1320

Ile Gly  Leu Pro Pro His Asn  Leu Thr Leu Thr Thr  Asp Arg Tyr
    1325                1330                1335

Asp Arg  Asp Ser Glu Gln Gln  Ile Arg Gln Gln Val  Ala Phe Ser
    1340                1345                1350

Asp Gly  Phe Gly Arg Leu Leu  Gln Ala Ser Val Arg  His Glu Ala
    1355                1360                1365

Gly Glu  Ala Trp Gln Arg Asn  Gln Asp Gly Ser Leu  Val Thr Lys
    1370                1375                1380

Val Glu  Asn Thr Lys Thr Arg  Trp Ala Val Thr Gly  Arg Thr Glu
    1385                1390                1395

Tyr Asp  Asn Lys Gly Gln Thr  Ile Arg Thr Tyr Gln  Pro Tyr Phe
    1400                1405                1410

Leu Asn  Asp Trp Arg Tyr Val  Ser Asp Asp Ser Ala  Arg Lys Glu
    1415                1420                1425

Ala Tyr  Ala Asp Thr His Ile  Tyr Asp Pro Ile Gly  Arg Glu Ile
    1430                1435                1440

Arg Val  Ile Thr Ala Lys Gly  Trp Leu Arg Gln Ser  Gln Tyr Phe
    1445                1450                1455

Pro Trp  Phe Thr Val Ser Glu  Asp Glu Asn Asp Thr  Ala Ala Asp
    1460                1465                1470

Ala Leu  Val
    1475
```

<210> SEQ ID NO 5

-continued

<211> LENGTH: 2745
<212> TYPE: DNA
<213> ORGANISM: Photorhabdus luminescens
<220> FEATURE:
<221> NAME/KEY: CDS
<222> LOCATION: (1)..(2745)

<400> SEQUENCE: 5

```
atg agc agt tac aat tct gca att gac caa aag acc ccc tcg att aag       48
Met Ser Ser Tyr Asn Ser Ala Ile Asp Gln Lys Thr Pro Ser Ile Lys
1               5                   10                  15

gta tta gat aac agg aaa tta aat gta cgt act tta gaa tat cta cgc       96
Val Leu Asp Asn Arg Lys Leu Asn Val Arg Thr Leu Glu Tyr Leu Arg
            20                  25                  30

act caa gct gac gaa aac agt gat gaa tta att acg ttc tat gag ttc      144
Thr Gln Ala Asp Glu Asn Ser Asp Glu Leu Ile Thr Phe Tyr Glu Phe
        35                  40                  45

aat att ccg gga ttt cag gta aaa agc acc gat cct cgt aaa aat aaa      192
Asn Ile Pro Gly Phe Gln Val Lys Ser Thr Asp Pro Arg Lys Asn Lys
    50                  55                  60

aac cag agc ggc cca aat ttc att cgt gtc ttt aat ctt gcc ggt caa      240
Asn Gln Ser Gly Pro Asn Phe Ile Arg Val Phe Asn Leu Ala Gly Gln
65                  70                  75                  80

gtt tta cgt gaa gaa agt gtt gat gcc ggt cgg act att acc ctc aat      288
Val Leu Arg Glu Glu Ser Val Asp Ala Gly Arg Thr Ile Thr Leu Asn
                85                  90                  95

gat att gaa agt cgc ccg gtg ttg atc atc aat gca acc ggt gtc cgc      336
Asp Ile Glu Ser Arg Pro Val Leu Ile Ile Asn Ala Thr Gly Val Arg
            100                 105                 110

caa aac cat cgt tat gaa gat aac acc ctt ccc ggt cgt ctg ctc gct      384
Gln Asn His Arg Tyr Glu Asp Asn Thr Leu Pro Gly Arg Leu Leu Ala
        115                 120                 125

atc acc gaa caa gta cag gca gga gag aaa acg acc gaa cgt ctt atc      432
Ile Thr Glu Gln Val Gln Ala Gly Glu Lys Thr Thr Glu Arg Leu Ile
    130                 135                 140

tgg gcc ggc aat acg ccg caa gaa aaa gat tac aac ctc gcc ggt cag      480
Trp Ala Gly Asn Thr Pro Gln Glu Lys Asp Tyr Asn Leu Ala Gly Gln
145                 150                 155                 160

tgt gtc cgc cat tac gat acc gcg gga ctt act caa ctc aat agc ctt      528
Cys Val Arg His Tyr Asp Thr Ala Gly Leu Thr Gln Leu Asn Ser Leu
                165                 170                 175

tct ctg gct ggc gtc gtg cta tca caa tct caa caa ctg ctt acc gat      576
Ser Leu Ala Gly Val Val Leu Ser Gln Ser Gln Gln Leu Leu Thr Asp
            180                 185                 190

aac cag gat gcc gac tgg aca ggt gaa gac cag agc ctc tgg caa caa      624
Asn Gln Asp Ala Asp Trp Thr Gly Glu Asp Gln Ser Leu Trp Gln Gln
        195                 200                 205

aaa ctg agt agt gat gtc tat atc acc caa agt aac act gat gcc acc      672
Lys Leu Ser Ser Asp Val Tyr Ile Thr Gln Ser Asn Thr Asp Ala Thr
    210                 215                 220

ggg gct tta ctg acc cag acc gat gcc aaa ggc aac att cag cgg ctg      720
Gly Ala Leu Leu Thr Gln Thr Asp Ala Lys Gly Asn Ile Gln Arg Leu
225                 230                 235                 240

gcc tat gat gtg gcc ggg cag cta aaa ggg agt tgg tta aca ctc aaa      768
Ala Tyr Asp Val Ala Gly Gln Leu Lys Gly Ser Trp Leu Thr Leu Lys
                245                 250                 255

ggt cag gcg gaa cag gtg att atc aaa tcg cta acc tac tcc gcc gcc      816
Gly Gln Ala Glu Gln Val Ile Ile Lys Ser Leu Thr Tyr Ser Ala Ala
            260                 265                 270

ggg caa aaa tta cgt gaa gag cac ggt aac ggg att gtc act gaa tac      864
Gly Gln Lys Leu Arg Glu Glu His Gly Asn Gly Ile Val Thr Glu Tyr
```

-continued

```
        275                 280                 285

agc tac gaa ccg gaa acc caa cgg ctt atc ggc att acc act cgc cgt      912
Ser Tyr Glu Pro Glu Thr Gln Arg Leu Ile Gly Ile Thr Thr Arg Arg
    290                 295                 300

cca tca gac gcc aag gtg ttg caa gac cta cgc tat caa tat gac cca      960
Pro Ser Asp Ala Lys Val Leu Gln Asp Leu Arg Tyr Gln Tyr Asp Pro
305                 310                 315                 320

gta ggc aat gtc att aat atc cgt aat gat gcg gaa gcc act cgc ttt     1008
Val Gly Asn Val Ile Asn Ile Arg Asn Asp Ala Glu Ala Thr Arg Phe
                325                 330                 335

tgg cgc aat cag aaa gta gcc ccg gag aat agc tat acc tac gat tcc     1056
Trp Arg Asn Gln Lys Val Ala Pro Glu Asn Ser Tyr Thr Tyr Asp Ser
            340                 345                 350

ctg tat cag ctt atc agc gcc acc ggg cgc gaa atg gcc aat atc ggt     1104
Leu Tyr Gln Leu Ile Ser Ala Thr Gly Arg Glu Met Ala Asn Ile Gly
        355                 360                 365

cag caa aac aac caa ctt ccc tcc cct gcg cta cct tct gac aac aat     1152
Gln Gln Asn Asn Gln Leu Pro Ser Pro Ala Leu Pro Ser Asp Asn Asn
    370                 375                 380

acc tac act aac tat act cgc agc tac agc tat gat cac agt ggt aat     1200
Thr Tyr Thr Asn Tyr Thr Arg Ser Tyr Ser Tyr Asp His Ser Gly Asn
385                 390                 395                 400

ctg acg caa att cgg cac agc tcg cca gct acc cag aac aac tac acc     1248
Leu Thr Gln Ile Arg His Ser Ser Pro Ala Thr Gln Asn Asn Tyr Thr
                405                 410                 415

gtg gct atc acc ctc tca aac cgc agc aat cgg ggt gtt ctc agt acg     1296
Val Ala Ile Thr Leu Ser Asn Arg Ser Asn Arg Gly Val Leu Ser Thr
            420                 425                 430

cta acc acc gat cca aat caa gtg gat acg ttg ttt gat gcc ggt ggt     1344
Leu Thr Thr Asp Pro Asn Gln Val Asp Thr Leu Phe Asp Ala Gly Gly
        435                 440                 445

cac caa acc agt tta tta ccc gga cag aca ctt atc tgg aca cca cga     1392
His Gln Thr Ser Leu Leu Pro Gly Gln Thr Leu Ile Trp Thr Pro Arg
    450                 455                 460

gga gag tta aag cag gtt aat aat ggc ccg gga aat gag tgg tac cgc     1440
Gly Glu Leu Lys Gln Val Asn Asn Gly Pro Gly Asn Glu Trp Tyr Arg
465                 470                 475                 480

tac gac agc aac ggc atg aga caa ctg aaa gtg agt gaa cag cca acc     1488
Tyr Asp Ser Asn Gly Met Arg Gln Leu Lys Val Ser Glu Gln Pro Thr
                485                 490                 495

cag aat act acg cag caa caa cgg gta atc tat ttg ccg gga ctg gag     1536
Gln Asn Thr Thr Gln Gln Gln Arg Val Ile Tyr Leu Pro Gly Leu Glu
            500                 505                 510

cta cgc aca acc cag agc aac gcc aca aca acg gaa gag tta cac gtt     1584
Leu Arg Thr Thr Gln Ser Asn Ala Thr Thr Thr Glu Glu Leu His Val
        515                 520                 525

atc aca ctc ggt gaa gcc ggt cgc gca cag gta cgg gtg ttg cac tgg     1632
Ile Thr Leu Gly Glu Ala Gly Arg Ala Gln Val Arg Val Leu His Trp
    530                 535                 540

gag agc ggt aag cca gaa gat gtc aac aat aat caa cta cgt tac agc     1680
Glu Ser Gly Lys Pro Glu Asp Val Asn Asn Asn Gln Leu Arg Tyr Ser
545                 550                 555                 560

tac gat aat ctg atc ggc tcc agc cag ctt gaa ctg gac aac caa gga     1728
Tyr Asp Asn Leu Ile Gly Ser Ser Gln Leu Glu Leu Asp Asn Gln Gly
                565                 570                 575

caa att atc agc gag gaa gag tat tat cca ttt ggc ggg aca gcg ctg     1776
Gln Ile Ile Ser Glu Glu Glu Tyr Tyr Pro Phe Gly Gly Thr Ala Leu
            580                 585                 590

tgg gca gca aac agc caa aca gaa gcc agc tat aaa acg att cgc tat     1824
```

-continued

Trp Ala Ala Asn Ser Gln Thr Glu Ala Ser Tyr Lys Thr Ile Arg Tyr
595 600 605 tcc ggc aaa gaa cga gat gcc acc ggg ttg tat tat tac ggt tat cgt 1872
Ser Gly Lys Glu Arg Asp Ala Thr Gly Leu Tyr Tyr Tyr Gly Tyr Arg
610 615 620 tat tac caa ccg tgg gcg ggc aga tgg tta agc gcg gac ccg gca gga 1920
Tyr Tyr Gln Pro Trp Ala Gly Arg Trp Leu Ser Ala Asp Pro Ala Gly
625 630 635 640 acc att gat ggg ctg aat cta tac cga atg gta aga aat aat cct gtg 1968
Thr Ile Asp Gly Leu Asn Leu Tyr Arg Met Val Arg Asn Asn Pro Val
645 650 655 agt tta caa gat gaa aat gga tta gcg cca gaa aaa ggg aaa tat acc 2016
Ser Leu Gln Asp Glu Asn Gly Leu Ala Pro Glu Lys Gly Lys Tyr Thr
660 665 670 aaa gag gta aat ttc ttt gat gaa tta aaa ttc aaa ttg gca gcc aaa 2064
Lys Glu Val Asn Phe Phe Asp Glu Leu Lys Phe Lys Leu Ala Ala Lys
675 680 685 agt tca cat gtt gtc aaa tgg aac gag aaa gag agc agt tat aca aaa 2112
Ser Ser His Val Val Lys Trp Asn Glu Lys Glu Ser Ser Tyr Thr Lys
690 695 700 aat aaa tca ttg aaa gtg gtt cgt gtc ggt gat tcc gat ccg tcg ggt 2160
Asn Lys Ser Leu Lys Val Val Arg Val Gly Asp Ser Asp Pro Ser Gly
705 710 715 720 tat ttg cta agc cac gaa gag tta cta aaa ggt ata gaa aaa agt caa 2208
Tyr Leu Leu Ser His Glu Glu Leu Leu Lys Gly Ile Glu Lys Ser Gln
725 730 735 atc ata tat agc cga ctt gaa gaa aac agc tcc ctt tca gaa aaa tca 2256
Ile Ile Tyr Ser Arg Leu Glu Glu Asn Ser Ser Leu Ser Glu Lys Ser
740 745 750 aaa acg aat ctt tct tta gga tct gaa ata tcc ggt tat atg gca aga 2304
Lys Thr Asn Leu Ser Leu Gly Ser Glu Ile Ser Gly Tyr Met Ala Arg
755 760 765 acc ata caa gat acg ata tca gaa tat gcc gaa gag cat aaa tat aga 2352
Thr Ile Gln Asp Thr Ile Ser Glu Tyr Ala Glu Glu His Lys Tyr Arg
770 775 780 agt aat cac cct gat ttt tat tca gaa acc gat ttc ttt gcg tta atg 2400
Ser Asn His Pro Asp Phe Tyr Ser Glu Thr Asp Phe Phe Ala Leu Met
785 790 795 800 gat aaa agt gaa aaa aat gat tat tcc ggt gaa aga aaa att tat gcg 2448
Asp Lys Ser Glu Lys Asn Asp Tyr Ser Gly Glu Arg Lys Ile Tyr Ala
805 810 815 gca atg gag gtt aag gtt tat cat gat tta aaa aat aaa caa tca gaa 2496
Ala Met Glu Val Lys Val Tyr His Asp Leu Lys Asn Lys Gln Ser Glu
820 825 830 tta cat gtc aac tat gca ttg gcc cat ccc tat acg caa ttg agt aat 2544
Leu His Val Asn Tyr Ala Leu Ala His Pro Tyr Thr Gln Leu Ser Asn
835 840 845 gaa gaa aga gcg ctg ttg caa gaa aca gaa ccc gct att gca ata gat 2592
Glu Glu Arg Ala Leu Leu Gln Glu Thr Glu Pro Ala Ile Ala Ile Asp
850 855 860 aga gaa tat aat ttc aaa ggt gtt ggc aaa ttc ctg aca atg aaa gca 2640
Arg Glu Tyr Asn Phe Lys Gly Val Gly Lys Phe Leu Thr Met Lys Ala
865 870 875 880 att aaa aaa tca ttg aaa gga cat aaa att aat agg ata tca aca gag 2688
Ile Lys Lys Ser Leu Lys Gly His Lys Ile Asn Arg Ile Ser Thr Glu
885 890 895 gct att aat att cgc tct gcg gct atc gct gag aat tta gga atg cgg 2736
Ala Ile Asn Ile Arg Ser Ala Ala Ile Ala Glu Asn Leu Gly Met Arg
900 905 910

-continued

```
aga act tca                                                       2745
Arg Thr Ser
        915


<210> SEQ ID NO 6
<211> LENGTH: 915
<212> TYPE: PRT
<213> ORGANISM: Photorhabdus luminescens

<400> SEQUENCE: 6

Met Ser Ser Tyr Asn Ser Ala Ile Asp Gln Lys Thr Pro Ser Ile Lys
1               5                   10                  15

Val Leu Asp Asn Arg Lys Leu Asn Val Arg Thr Leu Glu Tyr Leu Arg
            20                  25                  30

Thr Gln Ala Asp Glu Asn Ser Asp Glu Leu Ile Thr Phe Tyr Glu Phe
        35                  40                  45

Asn Ile Pro Gly Phe Gln Val Lys Ser Thr Asp Pro Arg Lys Asn Lys
    50                  55                  60

Asn Gln Ser Gly Pro Asn Phe Ile Arg Val Phe Asn Leu Ala Gly Gln
65                  70                  75                  80

Val Leu Arg Glu Glu Ser Val Asp Ala Gly Arg Thr Ile Thr Leu Asn
                85                  90                  95

Asp Ile Glu Ser Arg Pro Val Leu Ile Ile Asn Ala Thr Gly Val Arg
            100                 105                 110

Gln Asn His Arg Tyr Glu Asp Asn Thr Leu Pro Gly Arg Leu Leu Ala
        115                 120                 125

Ile Thr Glu Gln Val Gln Ala Gly Glu Lys Thr Thr Glu Arg Leu Ile
    130                 135                 140

Trp Ala Gly Asn Thr Pro Gln Glu Lys Asp Tyr Asn Leu Ala Gly Gln
145                 150                 155                 160

Cys Val Arg His Tyr Asp Thr Ala Gly Leu Thr Gln Leu Asn Ser Leu
                165                 170                 175

Ser Leu Ala Gly Val Val Leu Ser Gln Ser Gln Gln Leu Leu Thr Asp
            180                 185                 190

Asn Gln Asp Ala Asp Trp Thr Gly Glu Asp Gln Ser Leu Trp Gln Gln
        195                 200                 205

Lys Leu Ser Ser Asp Val Tyr Ile Thr Gln Ser Asn Thr Asp Ala Thr
    210                 215                 220

Gly Ala Leu Leu Thr Gln Thr Asp Ala Lys Gly Asn Ile Gln Arg Leu
225                 230                 235                 240

Ala Tyr Asp Val Ala Gly Gln Leu Lys Gly Ser Trp Leu Thr Leu Lys
                245                 250                 255

Gly Gln Ala Glu Gln Val Ile Ile Lys Ser Leu Thr Tyr Ser Ala Ala
            260                 265                 270

Gly Gln Lys Leu Arg Glu Glu His Gly Asn Gly Ile Val Thr Glu Tyr
        275                 280                 285

Ser Tyr Glu Pro Glu Thr Gln Arg Leu Ile Gly Ile Thr Thr Arg Arg
    290                 295                 300

Pro Ser Asp Ala Lys Val Leu Gln Asp Leu Arg Tyr Gln Tyr Asp Pro
305                 310                 315                 320

Val Gly Asn Val Ile Asn Ile Arg Asn Asp Ala Glu Ala Thr Arg Phe
                325                 330                 335

Trp Arg Asn Gln Lys Val Ala Pro Glu Asn Ser Tyr Thr Tyr Asp Ser
            340                 345                 350

Leu Tyr Gln Leu Ile Ser Ala Thr Gly Arg Glu Met Ala Asn Ile Gly
```

-continued

```
        355                 360                 365

Gln Gln Asn Asn Gln Leu Pro Ser Pro Ala Leu Pro Ser Asp Asn Asn
    370                 375                 380

Thr Tyr Thr Asn Tyr Thr Arg Ser Tyr Ser Tyr Asp His Ser Gly Asn
385                 390                 395                 400

Leu Thr Gln Ile Arg His Ser Ser Pro Ala Thr Gln Asn Asn Tyr Thr
                405                 410                 415

Val Ala Ile Thr Leu Ser Asn Arg Ser Asn Arg Gly Val Leu Ser Thr
            420                 425                 430

Leu Thr Thr Asp Pro Asn Gln Val Asp Thr Leu Phe Asp Ala Gly Gly
        435                 440                 445

His Gln Thr Ser Leu Leu Pro Gly Gln Thr Leu Ile Trp Thr Pro Arg
    450                 455                 460

Gly Glu Leu Lys Gln Val Asn Asn Gly Pro Gly Asn Glu Trp Tyr Arg
465                 470                 475                 480

Tyr Asp Ser Asn Gly Met Arg Gln Leu Lys Val Ser Glu Gln Pro Thr
                485                 490                 495

Gln Asn Thr Thr Gln Gln Gln Arg Val Ile Tyr Leu Pro Gly Leu Glu
            500                 505                 510

Leu Arg Thr Thr Gln Ser Asn Ala Thr Thr Thr Glu Glu Leu His Val
        515                 520                 525

Ile Thr Leu Gly Glu Ala Gly Arg Ala Gln Val Arg Val Leu His Trp
    530                 535                 540

Glu Ser Gly Lys Pro Glu Asp Val Asn Asn Asn Gln Leu Arg Tyr Ser
545                 550                 555                 560

Tyr Asp Asn Leu Ile Gly Ser Ser Gln Leu Glu Leu Asp Asn Gln Gly
                565                 570                 575

Gln Ile Ile Ser Glu Glu Glu Tyr Tyr Pro Phe Gly Gly Thr Ala Leu
            580                 585                 590

Trp Ala Ala Asn Ser Gln Thr Glu Ala Ser Tyr Lys Thr Ile Arg Tyr
        595                 600                 605

Ser Gly Lys Glu Arg Asp Ala Thr Gly Leu Tyr Tyr Tyr Gly Tyr Arg
    610                 615                 620

Tyr Tyr Gln Pro Trp Ala Gly Arg Trp Leu Ser Ala Asp Pro Ala Gly
625                 630                 635                 640

Thr Ile Asp Gly Leu Asn Leu Tyr Arg Met Val Arg Asn Asn Pro Val
                645                 650                 655

Ser Leu Gln Asp Glu Asn Gly Leu Ala Pro Glu Lys Gly Lys Tyr Thr
            660                 665                 670

Lys Glu Val Asn Phe Phe Asp Glu Leu Lys Phe Lys Leu Ala Ala Lys
        675                 680                 685

Ser Ser His Val Val Lys Trp Asn Glu Lys Glu Ser Ser Tyr Thr Lys
    690                 695                 700

Asn Lys Ser Leu Lys Val Val Arg Val Gly Asp Ser Asp Pro Ser Gly
705                 710                 715                 720

Tyr Leu Leu Ser His Glu Glu Leu Leu Lys Gly Ile Glu Lys Ser Gln
                725                 730                 735

Ile Ile Tyr Ser Arg Leu Glu Glu Asn Ser Ser Leu Ser Glu Lys Ser
            740                 745                 750

Lys Thr Asn Leu Ser Leu Gly Ser Glu Ile Ser Gly Tyr Met Ala Arg
        755                 760                 765

Thr Ile Gln Asp Thr Ile Ser Glu Tyr Ala Glu Glu His Lys Tyr Arg
    770                 775                 780
```

-continued

```
Ser Asn His Pro Asp Phe Tyr Ser Glu Thr Asp Phe Phe Ala Leu Met
785                 790                 795                 800

Asp Lys Ser Glu Lys Asn Asp Tyr Ser Gly Glu Arg Lys Ile Tyr Ala
                805                 810                 815

Ala Met Glu Val Lys Val Tyr His Asp Leu Lys Asn Lys Gln Ser Glu
            820                 825                 830

Leu His Val Asn Tyr Ala Leu Ala His Pro Tyr Thr Gln Leu Ser Asn
        835                 840                 845

Glu Glu Arg Ala Leu Leu Gln Glu Thr Glu Pro Ala Ile Ala Ile Asp
    850                 855                 860

Arg Glu Tyr Asn Phe Lys Gly Val Gly Lys Phe Leu Thr Met Lys Ala
865                 870                 875                 880

Ile Lys Lys Ser Leu Lys Gly His Lys Ile Asn Arg Ile Ser Thr Glu
                885                 890                 895

Ala Ile Asn Ile Arg Ser Ala Ala Ile Ala Glu Asn Leu Gly Met Arg
            900                 905                 910

Arg Thr Ser
        915


<210> SEQ ID NO 7
<211> LENGTH: 7512
<212> TYPE: DNA
<213> ORGANISM: Photorhabdus luminescens

<400> SEQUENCE: 7

atgcaaaact cattatcaag cactatcgat actatttgtc agaaactgca attaacttgt     60

ccggcggaaa ttgctttgta tccctttgat actttccggg aaaaaactcg gggaatggtt    120

aattgggggg aagcaaaacg gatttatgaa attgcacaag cggaacagga tagaaaccta    180

cttcatgaaa aacgtatttt tgcctatgct aatccgctgc tgaaaaacgc tgttcggttg    240

ggtacccggc aaatgttggg ttttatacaa ggttatagtg atctgtttgg taatcgtgct    300

gataactatg ccgcgccggg ctcggttgca tcgatgttct caccggcggc ttatttgacg    360

gaattgtacc gtgaagccaa aaacttgcat gacagcagct caatttatta cctagataaa    420

cgtcgcccgg atttagcaag cttaatgctc agccagaaaa atatggatga ggaaatttca    480

acgctggctc tctctaatga attgtgcctt gccgggatcg aaacaaaaac aggaaaatca    540

caagatgaag tgatggatat gttgtcaact tatcgtttaa gtggagagac accttatcat    600

cacgcttatg aaactgttcg tgaaatcgtt catgaacgtg atccaggatt tcgtcatttg    660

tcacaggcac ccattgttgc tgctaagctc gatcctgtga ctttgttggg tattagctcc    720

catatttcgc cagaactgta taacttgctg attgaggaga tcccggaaaa agatgaagcc    780

gcgcttgata cgctttataa aacaaacttt ggcgatatta ctactgctca gttaatgtcc    840

ccaagttatc tggcccggta ttatggcgtc tcaccggaag atattgccta cgtgacgact    900

tcattatcac atgttggata tagcagtgat attctggtta ttccgttggt cgatggtgtg    960

ggtaagatgg aagtagttcg tgttacccga acaccatcgg ataattatac cagtcagacg   1020

aattatattg agctgtatcc acagggtggc gacaattatt tgatcaaata caatctaagc   1080

aatagttttg gtttggatga tttttatctg caatataaag atggttccgc tgattggact   1140

gagattgccc ataatcccta tcctgatatg gtcataaatc aaaagtatga atcacaggcg   1200

acaatcaaac gtagtgactc tgacaatata ctcagtatag ggttacaaag atggcatagc   1260

ggtagttata attttgccgc cgccaatttt aaaattgacc aatactcccc gaaagctttc   1320
```

-continued

```
ctgcttaaaa tgaataaggc tattcggttg ctcaaagcta ccggcctctc ttttgctacg   1380
ttggagcgta ttgttgatag tgttaatagc accaaatcca tcacggttga ggtattaaac   1440
aaggtttatc gggtaaaatt ctatattgat cgttatggca tcagtgaaga gacagccgct   1500
attttggcta atattaatat ctctcagcaa gctgttggca atcagcttag ccagtttgag   1560
caactattta atcacccgcc gctcaatggt attcgctatg aaatcagtga ggacaactcc   1620
aaacatcttc ctaatcctga tctgaacctt aaaccagaca gtaccggtga tgatcaacgc   1680
aaggcggttt taaaacgcgc gtttcaggtt aacgccagtg agttgtatca gatgttattg   1740
atcactgatc gtaaagaaga cggtgttatc aaaaataact tagagaattt gtctgatctg   1800
tatttggtta gtttgctggc ccagattcat aacctgacta ttgctgaatt gaacattttg   1860
ttggtgattt gtggctatgg cgacaccaac atttatcaga ttaccgacga taatttagcc   1920
aaaatagtgg aaacattgtt gtggatcact caatggttga agacccaaaa atggacagtt   1980
accgacctgt ttctgatgac cacggccact tacagcacca ctttaacgcc agaaattagc   2040
aatctgacgg ctacgttgtc ttcaactttg catggcaaag agagtctgat tggggaagat   2100
ctgaaaagag caatggcgcc ttgcttcact tcggctttgc atttgacttc tcaagaagtt   2160
gcgtatgacc tgctgttgtg gatagaccag attcaaccgg cacaaataac tgttgatggg   2220
ttttgggaag aagtgcaaac aacaccaacc agcttgaagg tgattacctt tgctcaggtg   2280
ctggcacaat tgagcctgat ctatcgtcgt attgggttaa gtgaaacgga actgtcactg   2340
atcgtgactc aatcttctct gctagtggca ggcaaaagca tactggatca cggtctgtta   2400
accctgatgg ccttggaagg ttttcatacc tgggttaatg gcttggggca acatgcctcc   2460
ttgatattgg cggcgttgaa agacggagcc ttgacagtta ccgatgtagc acaagctatg   2520
aataaggagg aatctctcct acaaatggca gctaatcagg tggagaagga tctaacaaaa   2580
ctgaccagtt ggacacagat tgacgctatt ctgcaatggt tacagatgtc ttcggccttg   2640
gcggtttctc cactggatct ggcagggatg atggccctga aatatgggat agatcataac   2700
tatgctgcct ggcaagctgc ggcggctgcg ctgatggctg atcatgctaa tcaggcacag   2760
aaaaaactgg atgagacgtt cagtaaggca ttatgtaact attatattaa tgctgttgtc   2820
gatagtgctg ctggagtacg tgatcgtaac ggtttatata cctatttgct gattgataat   2880
caggtttctg ccgatgtgat cacttcacgt attgcagaag ctatcgccgg tattcaactg   2940
tacgttaacc gggctttaaa ccgagatgaa ggtcagcttg catcggacgt tagtacccgt   3000
cagttcttca ctgactggga acgttacaat aaacgttaca gtacttgggc tggtgtctct   3060
gaactggtct attatccaga aaactatgtt gatcccactc agcgcattgg gcaaaccaaa   3120
atgatggatg cgctgttgca atccatcaac cagagccagc taaatgcgga tacggtggaa   3180
gatgctttca aaacttattt gaccagcttt gagcaggtag caaatctgaa agtaattagt   3240
gcttaccacg ataatgtgaa tgtggatcaa ggattaactt attttatcgg tatcgaccaa   3300
gcagctccgg gtacgtatta ctggcgtagt gttgatcaca gcaaatgtga aaatggcaag   3360
tttgccgcta atgcttgggg tgagtggaat aaaattacct gtgctgtcaa tccttggaaa   3420
aatatcatcc gtccggttgt ttatatgtcc cgcttatatc tgctatggct ggagcagcaa   3480
tcaaagaaaa gtgatgatgg taaaaccacg atttatcaat ataacttaaa actggctcat   3540
attcgttacg acggtagttg gaatacacca tttacttttg atgtgacaga aaaggtaaaa   3600
aattacacgt cgagtactga tgctgctgaa tctttagggt tgtattgtac tggttatcaa   3660
```

-continued

```
ggggaagaca ctctattagt tatgttctat tcgatgcaga gtagttatag ctcctatacc   3720
gataataatg cgccggtcac tgggctatat attttcgctg atatgtcatc agacaatatg   3780
acgaatgcac aagcaactaa ctattggaat aacagttatc cgcaatttga tactgtgatg   3840
gcagatccgg atagcgacaa taaaaaagtc ataaccagaa gagttaataa ccgttatgcg   3900
gaggattatg aaattccttc ctctgtgaca agtaacagta attattcttg ggtgatcac    3960
agtttaacca tgctttatgg tggtagtgtt cctaatatta cttttgaatc ggcggcagaa   4020
gatttaaggc tatctaccaa tatggcattg agtattattc ataatggata tgcgggaacc   4080
cgccgtatac aatgtaatct tatgaaacaa tacgcttcat taggtgataa atttataatt   4140
tatgattcat catttgatga tgcaaaccgt tttaatctgg tgccattgtt taaattcgga   4200
aaagacgaga actcagatga tagtatttgt atatataatg aaaacccttc ctctgaagat   4260
aagaagtggt atttttcttc gaaagatgac aataaaacag cggattataa tggtggaact   4320
caatgtatag atgctggaac cagtaacaaa gatttttatt ataatctcca ggagattgaa   4380
gtaattagtg ttactggtgg gtattggtcg agttataaaa tatccaaccc gattaatatc   4440
aatacgggca ttgatagtgc taaagtaaaa gtcaccgtaa aagcgggtgg tgacgatcaa   4500
atctttactg ctgataatag tacctatgtt cctcagcaac cggcacccag ttttgaggag   4560
atgatttatc agttcaataa cctgacaata gattgtaaga atttaaattt catcgacaat   4620
caggcacata ttgagattga tttcaccgct acggcacaag atggccgatt cttgggtgca   4680
gaaactttta ttatcccggt aactaaaaaa gttctcggta ctgagaacgt gattgcgtta   4740
tatagcgaaa ataacggtgt tcaatatatg caaattggcg catatcgtac ccgtttgaat   4800
acgttattcg ctcaacagtt ggttagccgt gctaatcgtg gcattgatgc agtgctcagt   4860
atggaaactc agaatattca ggaaccgcaa ttaggagcgg gcacatatgt gcagcttgtg   4920
ttggataaat atgatgagtc tattcatggc actaataaaa gctttgctat tgaatatgtt   4980
gatatattta aagagaacga tagttttgtg atttatcaag gagaacttag cgaaacaagt   5040
caaactgttg tgaaagtttt cttatcctat tttatagagg cgactggaaa taagaaccac   5100
ttatgggtac gtgctaaata ccaaaaggaa acgactgata agatcttgtt cgaccgtact   5160
gatgagaaag atccgcacgg ttggtttctc agcgacgatc acaagacctt tagtggtctc   5220
tcttccgcac aggcattaaa gaacgacagt gaaccgatgg atttctctgg cgccaatgct   5280
ctctatttct gggaactgtt ctattacacg ccgatgatga tggctcatcg tttgttgcag   5340
gaacagaatt ttgatgcggc gaaccattgg ttccgttatg tctggagtcc atccggttat   5400
atcgttgatg gtaaaattgc tatctaccac tggaacgtgc gaccgctgga agaagacacc   5460
agttggaatg cacaacaact ggactccacc gatccagatg ctgtagccca agatgatccg   5520
atgcactaca aggtggctac ctttatggcg acgttggatc tgctaatggc ccgtggtgat   5580
gctgcttacc gccagttaga gcgtgatacg ttggctgaag ctaaaatgtg gtatacacag   5640
gcgcttaatc tgttgggtga tgagccacaa gtgatgctga gtacgacttg ggctaatcca   5700
acattgggta atgctgcttc aaaaaccaca cagcaggttc gtcagcaagt gcttacccag   5760
ttgcgtctca atagcagggt aaaaaccccg ttgctaggaa cagccaattc cctgaccgct   5820
ttattcctgc cgcaggaaaa tagcaagctc aaaggctact ggcggacact ggcgcagcgt   5880
atgtttaatt tacgtcataa tctgtcgatt gacggccagc cgctctcctt gccgctgtat   5940
gctaaaccgg ctgatccaaa agctttactg agtgcggcgg tttcagcttc tcaaggggga   6000
gccgacttgc cgaaggcgcc gctgactatt caccgcttcc ctcaaatgct agaaggggca   6060
```

-continued

```
cggggcttgg ttaaccagct tatacagttc ggtagttcac tattggggta cagtgagcgt   6120

caggatgcgg aagctatgag tcaactactg caaacccaag ccagcgagtt aatactgacc   6180

agtattcgta tgcaggataa ccaattggca gagctggatt cggaaaaaac cgccttgcaa   6240

gtctctttag ctggagtgca acaacggttt gacagctata gccaactgta tgaggagaac   6300

atcaacgcag gtgagcagcg agcgctggcg ttacgctcag aatctgctat tgagtctcag   6360

ggagcgcaga tttcccgtat ggcaggcgcg ggtgttgata tggcaccaaa tatcttcggc   6420

ctggctgatg gcggcatgca ttatggtgct attgcctatg ccatcgctga cggtattgag   6480

ttgagtgctt ctgccaagat ggttgatgcg gagaaagttg ctcagtcgga aatatatcgc   6540

cgtcgccgtc aagaatggaa aattcagcgt gacaacgcac aagcggagat taaccagtta   6600

aacgcgcaac tggaatcact gtctattcgc cgtgaagccg ctgaaatgca aaaagagtac   6660

ctgaaaaccc agcaagctca ggcgcaggca caacttactt tcttaagaag caaattcagt   6720

aatcaagcgt tatatagttg gttacgaggg cgtttgtcag gtatttattt ccagttctat   6780

gacttggccg tatcacgttg cctgatggca gagcaatcct atcaatggga agctaatgat   6840

aattccatta gctttgtcaa accgggtgca tggcaaggaa cttacgccgg cttattgtgt   6900

ggagaagctt tgatacaaaa tctggcacaa atggaagagg catatctgaa atgggaatct   6960

cgcgctttgg aagtagaacg cacggtttca ttggcagtgg tttatgattc actggaaggt   7020

aatgatcgtt ttaatttagc ggaacaaata cctgcattat tggataaggg ggagggaaca   7080

gcaggaacta aagaaaatgg gttatcattg gctaatgcta tcctgtcagc ttcggtcaaa   7140

ttgtccgact tgaaactggg aacggattat ccagacagta tcgttggtag caacaaggtt   7200

cgtcgtatta agcaaatcag tgtttcgcta cctgcattgg ttgggcctta tcaggatgtt   7260

caggctatgc tcagctatgg tggcagtact caattgccga aaggttgttc agcgttggct   7320

gtgtctcatg gtaccaatga tagtggtcag ttccagttgg atttcaatga cggcaaatac   7380

ctgccatttg aaggtattgc tcttgatgat cagggtacac tgaatcttca atttccgaat   7440

gctaccgaca agcagaaagc aatattgcaa actatgagcg atattatttt gcatattcgt   7500

tataccatcc gt                                                       7512
```

<210> SEQ ID NO 8
<211> LENGTH: 2504
<212> TYPE: PRT
<213> ORGANISM: Photorhabdus luminescens

<400> SEQUENCE: 8

```
Met Gln Asn Ser Leu Ser Ser Thr Ile Asp Thr Ile Cys Gln Lys Leu
1               5                   10                  15

Gln Leu Thr Cys Pro Ala Glu Ile Ala Leu Tyr Pro Phe Asp Thr Phe
            20                  25                  30

Arg Glu Lys Thr Arg Gly Met Val Asn Trp Gly Glu Ala Lys Arg Ile
        35                  40                  45

Tyr Glu Ile Ala Gln Ala Glu Gln Asp Arg Asn Leu Leu His Glu Lys
    50                  55                  60

Arg Ile Phe Ala Tyr Ala Asn Pro Leu Leu Lys Asn Ala Val Arg Leu
65                  70                  75                  80

Gly Thr Arg Gln Met Leu Gly Phe Ile Gln Gly Tyr Ser Asp Leu Phe
                85                  90                  95

Gly Asn Arg Ala Asp Asn Tyr Ala Ala Pro Gly Ser Val Ala Ser Met
            100                 105                 110
```

-continued

```
Phe Ser Pro Ala Ala Tyr Leu Thr Glu Leu Tyr Arg Glu Ala Lys Asn
        115                 120                 125

Leu His Asp Ser Ser Ser Ile Tyr Tyr Leu Asp Lys Arg Arg Pro Asp
    130                 135                 140

Leu Ala Ser Leu Met Leu Ser Gln Lys Asn Met Asp Glu Glu Ile Ser
145                 150                 155                 160

Thr Leu Ala Leu Ser Asn Glu Leu Cys Leu Ala Gly Ile Glu Thr Lys
                165                 170                 175

Thr Gly Lys Ser Gln Asp Glu Val Met Asp Met Leu Ser Thr Tyr Arg
            180                 185                 190

Leu Ser Gly Glu Thr Pro Tyr His His Ala Tyr Glu Thr Val Arg Glu
        195                 200                 205

Ile Val His Glu Arg Asp Pro Gly Phe Arg His Leu Ser Gln Ala Pro
    210                 215                 220

Ile Val Ala Ala Lys Leu Asp Pro Val Thr Leu Leu Gly Ile Ser Ser
225                 230                 235                 240

His Ile Ser Pro Glu Leu Tyr Asn Leu Leu Ile Glu Glu Ile Pro Glu
                245                 250                 255

Lys Asp Glu Ala Ala Leu Asp Thr Leu Tyr Lys Thr Asn Phe Gly Asp
            260                 265                 270

Ile Thr Thr Ala Gln Leu Met Ser Pro Ser Tyr Leu Ala Arg Tyr Tyr
        275                 280                 285

Gly Val Ser Pro Glu Asp Ile Ala Tyr Val Thr Thr Ser Leu Ser His
    290                 295                 300

Val Gly Tyr Ser Ser Asp Ile Leu Val Ile Pro Leu Val Asp Gly Val
305                 310                 315                 320

Gly Lys Met Glu Val Val Arg Val Thr Arg Thr Pro Ser Asp Asn Tyr
                325                 330                 335

Thr Ser Gln Thr Asn Tyr Ile Glu Leu Tyr Pro Gln Gly Gly Asp Asn
            340                 345                 350

Tyr Leu Ile Lys Tyr Asn Leu Ser Asn Ser Phe Gly Leu Asp Asp Phe
        355                 360                 365

Tyr Leu Gln Tyr Lys Asp Gly Ser Ala Asp Trp Thr Glu Ile Ala His
    370                 375                 380

Asn Pro Tyr Pro Asp Met Val Ile Asn Gln Lys Tyr Glu Ser Gln Ala
385                 390                 395                 400

Thr Ile Lys Arg Ser Asp Ser Asp Asn Ile Leu Ser Ile Gly Leu Gln
                405                 410                 415

Arg Trp His Ser Gly Ser Tyr Asn Phe Ala Ala Ala Asn Phe Lys Ile
            420                 425                 430

Asp Gln Tyr Ser Pro Lys Ala Phe Leu Leu Lys Met Asn Lys Ala Ile
        435                 440                 445

Arg Leu Leu Lys Ala Thr Gly Leu Ser Phe Ala Thr Leu Glu Arg Ile
    450                 455                 460

Val Asp Ser Val Asn Ser Thr Lys Ser Ile Thr Val Glu Val Leu Asn
465                 470                 475                 480

Lys Val Tyr Arg Val Lys Phe Tyr Ile Asp Arg Tyr Gly Ile Ser Glu
                485                 490                 495

Glu Thr Ala Ala Ile Leu Ala Asn Ile Asn Ile Ser Gln Gln Ala Val
            500                 505                 510

Gly Asn Gln Leu Ser Gln Phe Glu Gln Leu Phe Asn His Pro Pro Leu
        515                 520                 525
```

-continued

```
Asn Gly Ile Arg Tyr Glu Ile Ser Glu Asp Asn Ser Lys His Leu Pro
    530                 535                 540

Asn Pro Asp Leu Asn Leu Lys Pro Asp Ser Thr Gly Asp Asp Gln Arg
545                 550                 555                 560

Lys Ala Val Leu Lys Arg Ala Phe Gln Val Asn Ala Ser Glu Leu Tyr
                565                 570                 575

Gln Met Leu Leu Ile Thr Asp Arg Lys Glu Asp Gly Val Ile Lys Asn
            580                 585                 590

Asn Leu Glu Asn Leu Ser Asp Leu Tyr Leu Val Ser Leu Leu Ala Gln
        595                 600                 605

Ile His Asn Leu Thr Ile Ala Glu Leu Asn Ile Leu Leu Val Ile Cys
    610                 615                 620

Gly Tyr Gly Asp Thr Asn Ile Tyr Gln Ile Thr Asp Asp Asn Leu Ala
625                 630                 635                 640

Lys Ile Val Glu Thr Leu Leu Trp Ile Thr Gln Trp Leu Lys Thr Gln
                645                 650                 655

Lys Trp Thr Val Thr Asp Leu Phe Leu Met Thr Thr Ala Thr Tyr Ser
            660                 665                 670

Thr Thr Leu Thr Pro Glu Ile Ser Asn Leu Thr Ala Thr Leu Ser Ser
        675                 680                 685

Thr Leu His Gly Lys Glu Ser Leu Ile Gly Glu Asp Leu Lys Arg Ala
    690                 695                 700

Met Ala Pro Cys Phe Thr Ser Ala Leu His Leu Thr Ser Gln Glu Val
705                 710                 715                 720

Ala Tyr Asp Leu Leu Leu Trp Ile Asp Gln Ile Gln Pro Ala Gln Ile
                725                 730                 735

Thr Val Asp Gly Phe Trp Glu Glu Val Gln Thr Thr Pro Thr Ser Leu
            740                 745                 750

Lys Val Ile Thr Phe Ala Gln Val Leu Ala Gln Leu Ser Leu Ile Tyr
        755                 760                 765

Arg Arg Ile Gly Leu Ser Glu Thr Glu Leu Ser Leu Ile Val Thr Gln
    770                 775                 780

Ser Ser Leu Leu Val Ala Gly Lys Ser Ile Leu Asp His Gly Leu Leu
785                 790                 795                 800

Thr Leu Met Ala Leu Glu Gly Phe His Thr Trp Val Asn Gly Leu Gly
                805                 810                 815

Gln His Ala Ser Leu Ile Leu Ala Ala Leu Lys Asp Gly Ala Leu Thr
            820                 825                 830

Val Thr Asp Val Ala Gln Ala Met Asn Lys Glu Glu Ser Leu Leu Gln
        835                 840                 845

Met Ala Ala Asn Gln Val Glu Lys Asp Leu Thr Lys Leu Thr Ser Trp
    850                 855                 860

Thr Gln Ile Asp Ala Ile Leu Gln Trp Leu Gln Met Ser Ser Ala Leu
865                 870                 875                 880

Ala Val Ser Pro Leu Asp Leu Ala Gly Met Met Ala Leu Lys Tyr Gly
                885                 890                 895

Ile Asp His Asn Tyr Ala Ala Trp Gln Ala Ala Ala Ala Ala Leu Met
            900                 905                 910

Ala Asp His Ala Asn Gln Ala Gln Lys Lys Leu Asp Glu Thr Phe Ser
        915                 920                 925

Lys Ala Leu Cys Asn Tyr Tyr Ile Asn Ala Val Val Asp Ser Ala Ala
    930                 935                 940

Gly Val Arg Asp Arg Asn Gly Leu Tyr Thr Tyr Leu Leu Ile Asp Asn
```

-continued

```
945                 950                 955                 960

Gln Val Ser Ala Asp Val Ile Thr Ser Arg Ile Ala Glu Ala Ile Ala
                965                 970                 975

Gly Ile Gln Leu Tyr Val Asn Arg Ala Leu Asn Arg Asp Glu Gly Gln
            980                 985                 990

Leu Ala Ser Asp Val Ser Thr Arg  Gln Phe Phe Thr Asp  Trp Glu Arg
        995                 1000                1005

Tyr Asn  Lys Arg Tyr Ser Thr  Trp Ala Gly Val Ser  Glu Leu Val
    1010                 1015                 1020

Tyr Tyr  Pro Glu Asn Tyr Val  Asp Pro Thr Gln Arg  Ile Gly Gln
    1025                 1030                 1035

Thr Lys  Met Met Asp Ala Leu  Leu Gln Ser Ile Asn  Gln Ser Gln
    1040                 1045                 1050

Leu Asn  Ala Asp Thr Val Glu  Asp Ala Phe Lys Thr  Tyr Leu Thr
    1055                 1060                 1065

Ser Phe  Glu Gln Val Ala Asn  Leu Lys Val Ile Ser  Ala Tyr His
    1070                 1075                 1080

Asp Asn  Val Asn Val Asp Gln  Gly Leu Thr Tyr Phe  Ile Gly Ile
    1085                 1090                 1095

Asp Gln  Ala Ala Pro Gly Thr  Tyr Tyr Trp Arg Ser  Val Asp His
    1100                 1105                 1110

Ser Lys  Cys Glu Asn Gly Lys  Phe Ala Ala Asn Ala  Trp Gly Glu
    1115                 1120                 1125

Trp Asn  Lys Ile Thr Cys Ala  Val Asn Pro Trp Lys  Asn Ile Ile
    1130                 1135                 1140

Arg Pro  Val Val Tyr Met Ser  Arg Leu Tyr Leu Leu  Trp Leu Glu
    1145                 1150                 1155

Gln Gln  Ser Lys Lys Ser Asp  Asp Gly Lys Thr Thr  Ile Tyr Gln
    1160                 1165                 1170

Tyr Asn  Leu Lys Leu Ala His  Ile Arg Tyr Asp Gly  Ser Trp Asn
    1175                 1180                 1185

Thr Pro  Phe Thr Phe Asp Val  Thr Glu Lys Val Lys  Asn Tyr Thr
    1190                 1195                 1200

Ser Ser  Thr Asp Ala Ala Glu  Ser Leu Gly Leu Tyr  Cys Thr Gly
    1205                 1210                 1215

Tyr Gln  Gly Glu Asp Thr Leu  Leu Val Met Phe Tyr  Ser Met Gln
    1220                 1225                 1230

Ser Ser  Tyr Ser Ser Tyr Thr  Asp Asn Asn Ala Pro  Val Thr Gly
    1235                 1240                 1245

Leu Tyr  Ile Phe Ala Asp Met  Ser Ser Asp Asn Met  Thr Asn Ala
    1250                 1255                 1260

Gln Ala  Thr Asn Tyr Trp Asn  Asn Ser Tyr Pro Gln  Phe Asp Thr
    1265                 1270                 1275

Val Met  Ala Asp Pro Asp Ser  Asp Asn Lys Lys Val  Ile Thr Arg
    1280                 1285                 1290

Arg Val  Asn Asn Arg Tyr Ala  Glu Asp Tyr Glu Ile  Pro Ser Ser
    1295                 1300                 1305

Val Thr  Ser Asn Ser Asn Tyr  Ser Trp Gly Asp His  Ser Leu Thr
    1310                 1315                 1320

Met Leu  Tyr Gly Gly Ser Val  Pro Asn Ile Thr Phe  Glu Ser Ala
    1325                 1330                 1335

Ala Glu  Asp Leu Arg Leu Ser  Thr Asn Met Ala Leu  Ser Ile Ile
    1340                 1345                 1350
```

-continued

```
His Asn Gly Tyr Ala Gly Thr Arg Arg Ile Gln Cys Asn Leu Met
    1355                1360                1365

Lys Gln Tyr Ala Ser Leu Gly Asp Lys Phe Ile Ile Tyr Asp Ser
    1370                1375                1380

Ser Phe Asp Asp Ala Asn Arg Phe Asn Leu Val Pro Leu Phe Lys
    1385                1390                1395

Phe Gly Lys Asp Glu Asn Ser Asp Asp Ser Ile Cys Ile Tyr Asn
    1400                1405                1410

Glu Asn Pro Ser Ser Glu Asp Lys Lys Trp Tyr Phe Ser Ser Lys
    1415                1420                1425

Asp Asp Asn Lys Thr Ala Asp Tyr Asn Gly Gly Thr Gln Cys Ile
    1430                1435                1440

Asp Ala Gly Thr Ser Asn Lys Asp Phe Tyr Tyr Asn Leu Gln Glu
    1445                1450                1455

Ile Glu Val Ile Ser Val Thr Gly Gly Tyr Trp Ser Ser Tyr Lys
    1460                1465                1470

Ile Ser Asn Pro Ile Asn Ile Asn Thr Gly Ile Asp Ser Ala Lys
    1475                1480                1485

Val Lys Val Thr Val Lys Ala Gly Gly Asp Asp Gln Ile Phe Thr
    1490                1495                1500

Ala Asp Asn Ser Thr Tyr Val Pro Gln Gln Pro Ala Pro Ser Phe
    1505                1510                1515

Glu Glu Met Ile Tyr Gln Phe Asn Asn Leu Thr Ile Asp Cys Lys
    1520                1525                1530

Asn Leu Asn Phe Ile Asp Asn Gln Ala His Ile Glu Ile Asp Phe
    1535                1540                1545

Thr Ala Thr Ala Gln Asp Gly Arg Phe Leu Gly Ala Glu Thr Phe
    1550                1555                1560

Ile Ile Pro Val Thr Lys Lys Val Leu Gly Thr Glu Asn Val Ile
    1565                1570                1575

Ala Leu Tyr Ser Glu Asn Asn Gly Val Gln Tyr Met Gln Ile Gly
    1580                1585                1590

Ala Tyr Arg Thr Arg Leu Asn Thr Leu Phe Ala Gln Gln Leu Val
    1595                1600                1605

Ser Arg Ala Asn Arg Gly Ile Asp Ala Val Leu Ser Met Glu Thr
    1610                1615                1620

Gln Asn Ile Gln Glu Pro Gln Leu Gly Ala Gly Thr Tyr Val Gln
    1625                1630                1635

Leu Val Leu Asp Lys Tyr Asp Glu Ser Ile His Gly Thr Asn Lys
    1640                1645                1650

Ser Phe Ala Ile Glu Tyr Val Asp Ile Phe Lys Glu Asn Asp Ser
    1655                1660                1665

Phe Val Ile Tyr Gln Gly Glu Leu Ser Glu Thr Ser Gln Thr Val
    1670                1675                1680

Val Lys Val Phe Leu Ser Tyr Phe Ile Glu Ala Thr Gly Asn Lys
    1685                1690                1695

Asn His Leu Trp Val Arg Ala Lys Tyr Gln Lys Glu Thr Thr Asp
    1700                1705                1710

Lys Ile Leu Phe Asp Arg Thr Asp Glu Lys Asp Pro His Gly Trp
    1715                1720                1725

Phe Leu Ser Asp Asp His Lys Thr Phe Ser Gly Leu Ser Ser Ala
    1730                1735                1740
```

-continued

```
Gln Ala  Leu Lys Asn Asp Ser  Glu Pro Met Asp Phe  Ser Gly Ala
    1745                 1750                 1755

Asn Ala  Leu Tyr Phe Trp Glu  Leu Phe Tyr Tyr Thr  Pro Met Met
    1760                 1765                 1770

Met Ala  His Arg Leu Leu Gln  Glu Gln Asn Phe Asp  Ala Ala Asn
    1775                 1780                 1785

His Trp  Phe Arg Tyr Val Trp  Ser Pro Ser Gly Tyr  Ile Val Asp
    1790                 1795                 1800

Gly Lys  Ile Ala Ile Tyr His  Trp Asn Val Arg Pro  Leu Glu Glu
    1805                 1810                 1815

Asp Thr  Ser Trp Asn Ala Gln  Gln Leu Asp Ser Thr  Asp Pro Asp
    1820                 1825                 1830

Ala Val  Ala Gln Asp Asp Pro  Met His Tyr Lys Val  Ala Thr Phe
    1835                 1840                 1845

Met Ala  Thr Leu Asp Leu Leu  Met Ala Arg Gly Asp  Ala Ala Tyr
    1850                 1855                 1860

Arg Gln  Leu Glu Arg Asp Thr  Leu Ala Glu Ala Lys  Met Trp Tyr
    1865                 1870                 1875

Thr Gln  Ala Leu Asn Leu Leu  Gly Asp Glu Pro Gln  Val Met Leu
    1880                 1885                 1890

Ser Thr  Thr Trp Ala Asn Pro  Thr Leu Gly Asn Ala  Ala Ser Lys
    1895                 1900                 1905

Thr Thr  Gln Gln Val Arg Gln  Gln Val Leu Thr Gln  Leu Arg Leu
    1910                 1915                 1920

Asn Ser  Arg Val Lys Thr Pro  Leu Leu Gly Thr Ala  Asn Ser Leu
    1925                 1930                 1935

Thr Ala  Leu Phe Leu Pro Gln  Glu Asn Ser Lys Leu  Lys Gly Tyr
    1940                 1945                 1950

Trp Arg  Thr Leu Ala Gln Arg  Met Phe Asn Leu Arg  His Asn Leu
    1955                 1960                 1965

Ser Ile  Asp Gly Gln Pro Leu  Ser Leu Pro Leu Tyr  Ala Lys Pro
    1970                 1975                 1980

Ala Asp  Pro Lys Ala Leu Leu  Ser Ala Ala Val Ser  Ala Ser Gln
    1985                 1990                 1995

Gly Gly  Ala Asp Leu Pro Lys  Ala Pro Leu Thr Ile  His Arg Phe
    2000                 2005                 2010

Pro Gln  Met Leu Glu Gly Ala  Arg Gly Leu Val Asn  Gln Leu Ile
    2015                 2020                 2025

Gln Phe  Gly Ser Ser Leu Leu  Gly Tyr Ser Glu Arg  Gln Asp Ala
    2030                 2035                 2040

Glu Ala  Met Ser Gln Leu Leu  Gln Thr Gln Ala Ser  Glu Leu Ile
    2045                 2050                 2055

Leu Thr  Ser Ile Arg Met Gln  Asp Asn Gln Leu Ala  Glu Leu Asp
    2060                 2065                 2070

Ser Glu  Lys Thr Ala Leu Gln  Val Ser Leu Ala Gly  Val Gln Gln
    2075                 2080                 2085

Arg Phe  Asp Ser Tyr Ser Gln  Leu Tyr Glu Glu Asn  Ile Asn Ala
    2090                 2095                 2100

Gly Glu  Gln Arg Ala Leu Ala  Leu Arg Ser Glu Ser  Ala Ile Glu
    2105                 2110                 2115

Ser Gln  Gly Ala Gln Ile Ser  Arg Met Ala Gly Ala  Gly Val Asp
    2120                 2125                 2130

Met Ala  Pro Asn Ile Phe Gly  Leu Ala Asp Gly Gly  Met His Tyr
```

-continued

```
    2135                2140                2145

Gly Ala  Ile Ala Tyr Ala Ile  Ala Asp Gly Ile Glu  Leu Ser Ala
    2150                2155                2160

Ser Ala  Lys Met Val Asp Ala  Glu Lys Val Ala Gln  Ser Glu Ile
    2165                2170                2175

Tyr Arg  Arg Arg Arg Gln Glu  Trp Lys Ile Gln Arg  Asp Asn Ala
    2180                2185                2190

Gln Ala  Glu Ile Asn Gln Leu  Asn Ala Gln Leu Glu  Ser Leu Ser
    2195                2200                2205

Ile Arg  Arg Glu Ala Ala Glu  Met Gln Lys Glu Tyr  Leu Lys Thr
    2210                2215                2220

Gln Gln  Ala Gln Ala Gln Ala  Gln Leu Thr Phe Leu  Arg Ser Lys
    2225                2230                2235

Phe Ser  Asn Gln Ala Leu Tyr  Ser Trp Leu Arg Gly  Arg Leu Ser
    2240                2245                2250

Gly Ile  Tyr Phe Gln Phe Tyr  Asp Leu Ala Val Ser  Arg Cys Leu
    2255                2260                2265

Met Ala  Glu Gln Ser Tyr Gln  Trp Glu Ala Asn Asp  Asn Ser Ile
    2270                2275                2280

Ser Phe  Val Lys Pro Gly Ala  Trp Gln Gly Thr Tyr  Ala Gly Leu
    2285                2290                2295

Leu Cys  Gly Glu Ala Leu Ile  Gln Asn Leu Ala Gln  Met Glu Glu
    2300                2305                2310

Ala Tyr  Leu Lys Trp Glu Ser  Arg Ala Leu Glu Val  Glu Arg Thr
    2315                2320                2325

Val Ser  Leu Ala Val Val Tyr  Asp Ser Leu Glu Gly  Asn Asp Arg
    2330                2335                2340

Phe Asn  Leu Ala Glu Gln Ile  Pro Ala Leu Leu Asp  Lys Gly Glu
    2345                2350                2355

Gly Thr  Ala Gly Thr Lys Glu  Asn Gly Leu Ser Leu  Ala Asn Ala
    2360                2365                2370

Ile Leu  Ser Ala Ser Val Lys  Leu Ser Asp Leu Lys  Leu Gly Thr
    2375                2380                2385

Asp Tyr  Pro Asp Ser Ile Val  Gly Ser Asn Lys Val  Arg Arg Ile
    2390                2395                2400

Lys Gln  Ile Ser Val Ser Leu  Pro Ala Leu Val Gly  Pro Tyr Gln
    2405                2410                2415

Asp Val  Gln Ala Met Leu Ser  Tyr Gly Gly Ser Thr  Gln Leu Pro
    2420                2425                2430

Lys Gly  Cys Ser Ala Leu Ala  Val Ser His Gly Thr  Asn Asp Ser
    2435                2440                2445

Gly Gln  Phe Gln Leu Asp Phe  Asn Asp Gly Lys Tyr  Leu Pro Phe
    2450                2455                2460

Glu Gly  Ile Ala Leu Asp Asp  Gln Gly Thr Leu Asn  Leu Gln Phe
    2465                2470                2475

Pro Asn  Ala Thr Asp Lys Gln  Lys Ala Ile Leu Gln  Thr Met Ser
    2480                2485                2490

Asp Ile  Ile Leu His Ile Arg  Tyr Thr Ile Arg
    2495                2500
```

DNA SEQUENCES FROM *PHOTORHABDUS LUMINESCENS*

RELATED APPLICATIONS

This application claims priority from U.S. Provisional Patent Application Ser. No. US 60/191,806 filed March 24, 2000.

This invention was made with United States government support awarded by the following agencies:

USDA 97-34340-3987

The United States has certain rights in this invention.

BACKGROUND OF THE INVENTION

As reported in W098/08932, protein toxins from the genus Photorhabdus have been shown to have oral toxicity against insects. The toxin complex produced by *Photorhabdus luminescens* (W-14), for example, has been shown to contain ten to fourteen proteins, and it is known that these are produced by expression of genes from four distinct genomic regions: tca, tcb, tcc, and tcd. WO98/08932 discloses nucleotide sequences for many of the native toxin genes.

Of the separate toxins isolated from *Photorhabdus luminescens* (W-14), those designated Toxin A and Toxin B have been the subject of focused investigation for their activity against target insect species of interest, for example corn rootworm. Toxin A is comprised of two different subunits. The native gene tcda (SEQ ID NO:1) encodes protoxin TcdA (see SEQ ID NO:1). As determined by mass spectrometry, TcdA is processed by one or more proteases to provide Toxin A. More specifically, TcdA is an approximately 282.9 kDA protein (2516 aa) that is processed to provide TcdAii, an approximately 208.2 kDA (1849 aa) protein encoded by nucleotides 265–5811 of SEQ ID NO:1, and TcdAiii, an approximately 63.5 kDA (579 aa) protein encoded by nucleotides 5812–7551 of SEQ ID NO:1.

WO 01/11029 discloses nucleotide sequences that encode TcdA and TcbA and have base compositions that have been altered from that of the native genes to make them more similar to plant genes. Also disclosed are transgenic plants that express Toxin A and Toxin B.

We have observed that heterologous expression of Toxin A does not afford the level of oral toxicity to insects that is observed for the native toxin. It would be very valuable if means could be found to enhance the level of toxicity of heterologously expressed Toxin A.

SUMMARY OF THE INVENTION

The present invention provides nucleotide sequences for two genes, tcdB and tccC2, from the tcd genomic region of *Photorhabdus luminescens* W-14. These sequences were not previously known. We have discovered that coexpression of tcdB and tccC2 with tcdA in heterologous hosts results in enhanced levels of oral insect toxicity compared to that obtained when tcdA is expressed alone in such heterologous hosts. Coexpression of tcdB and tccC2 with tcdA or tcbA, or with any other functionally equivalent toxin gene in the same family as tcdA and tcbA, to provide enhanced oral insect activity falls within the scope of the invention.

SUMMARY OF THE INVENTION

SEQ ID NO: 1 is the DNA sequence for tcdA from *Photorhabdus luminescens* W-14.

SEQ ID NO: 2 is the amino acid sequence for TcdA from *Photorhabdus luminescens* W-14.

SEQ ID NO: 3 is the DNA sequence for tcdB from *Photorhabdus luminescens* W-14.

SEQ ID NO: 4 is the amino acid sequence for TcdB from *Photorhabdus luminescens* W-14.

SEQ ID NO: 5 is the DNA sequence for tccC2 from *Photorhabdus luminescens* W-14.

SEQ ID NO: 6 is the amino acid sequence for TccC2 from from *Photorhabdus luminescens* W-14.

SEQ ID NO: 7 is the DNA sequence for tcbA from from *Photorhabdus luminescens* W-14.

SEQ ID NO: 8 is the amino acid sequence for TcbA from *Photorhabdus luminescens* W-14.

DETAILED DESCRIPTION OF THE INVENTION

It is preferred for the nucleic acids according to the invention to comprise at least one sequence chosen from (a) the sequences according to SEQ ID NOS: 3 and 5.

(b) at least 14 base pairs-long partial sequences of the sequences defined under (a), (c) sequences that hybridize with the sequences defined under (a), (d) sequences that are at least 70%, preferably 80% and even more preferred, 90% identical to the sequences defined under (a), (e) sequences that are at least 70%, preferably 80% and even more preferred, 90% similar to the sequences defined under (a), (f) sequences that complement the sequences defined under (a), and (g) sequences that due to the degeneracy of the genetic code, code for the same amino acid sequence as(i.e. are "isocoding" with) the sequences defined under (a) through (e).

The expression "hybridize" as used herein refers to hybridization under the following specified conditions: 5×SSC; blocking reagent (Roche Diagnostics Inc., Mannheim, Germany), 1%; N-lauroyl-sarcosine, 0.1%; SDS (sodium-dodecyl sulfate) 0.02%; hybridization temperature: 60° C.; first wash step: 2×SSC at 60° C.; second wash step: 2×SSC at 60° C.; preferred second wash step: 0.5×SSC at 60° C.; especially preferred second wash step: 0.2×SSC at 60° C.

"Identity" and "similarity" are scored by the GAP algorithm using the Blosum 62 protein scoring matrix (Wisconsin Package Version 9.0, Genetics Computer Group (GCG), Madison, Wis.).

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, additional copies of one or more of the nucleotide sequences are added to *Xenorhabdus nematophilus, Xenorhabdus poinarii,* or *Photorhabdus luminescens* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in-vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera Agrobacterium, Alcaligenes, Azospiriilum, Azotobacter, Bacillus, Ciavibacter, Enterobacter, Erwinia, Flavobacter, Klebsielia, Pseudomonas, Rhizobium, Serratia, Streptomyces and Xanthomonas. Symbiotic fungi, such as Trichoderma and Gliocladium are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli,* either in transcriptional or translational fusion, behind the tac or trc promoter. For the expression of operons encoding multiple ORFS, the simplest procedure is to insert the operon into a vector such as pKK2233 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely for example, on yeast vectors and include the use of Pichia, Saccharomyces and Kluyveromyces (Sreekrishna, In: industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et al., Biotechnology 8:135–139 (1990)).

Expression of the Nucleotide Sequences in Plant Tissue

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant, In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, Arabidopsis, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleotide sequences which have low GC contents may express poorly in plants due to the existence of ATTTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction.

For efficient initiation of translation, sequences adjacent to the initiating methionine may require modification. For example, they can be modified by the inclusion of sequences known to be effective in plants. Joshi has suggested an appropriate consensus for plants (NAR 15: 6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CAMV 35S and 19S promoters. The nucleotide sequences of this invention can also be expressed under the regulation of promoters that are chemically regulated. This enables the insecticidal toxins to be synthesized only when the crop plants are treated with the inducing chemicals.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells which need to synthesize the insecticidal toxins to kill the invading insect pest. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from Agrobacterium, E9 from rbcs). Any available terminator known to function in plants can be used in the context of this invention.

Numerous other sequences can be incorporated into expression cassettes described in this invention. These include sequences which have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093–1096 (1986)). For both direct gene transfer and Agrobacterium-mediated transfer, transformation is usually (but not necessarily) undertaken with a selectable or screenable marker which may provide resistance to an antibiotic (kanamycin, hygromycin or methotrexate) or a herbicide (Basta). Examples of such markers are neomycin phosphotransferase, hygromycin phosphotransferase, dihydrofolate reductase, phosphinothricin acetyltransferase, 2,2-dichloroproprionic acid dehalogenase, acetohydroxyacid synthase, 5-enolpyruvylshikimate-phosphate synthase, haloarylnitrilase, protoporhyrinogen oxidase, acetyl-coenzyme A carboxylase, dihydropteroate synthase, chloramphenicol acetyl transferase, and •-glucuronidase. The choice of selectable or screenable marker for plant transformation is not, however, critical to the invention.

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., BioTechniques 4.,320–334 (1986)), electroporation (Riggs et al., Proc. Natl. Acad, Sci. USA 83.,5602–5606 (1986), Agrobacterium-mediated transformation (Hinchee et al., Biotechnology 6:915–921 (1988); See also, Ishida et al., Nature Biotechnology 14:745–750 (June 1996) (for maize transformation), direct gene transfer (Paszkowski et al., EMBO J. 3.2717–2722 (1984); Hayashimoto et al., Plant Physiol 93.857–863 (1990)(rice), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6.923–926 (1988)). See also, Weissinger et al., Annual Rev Genet. 22.13 421–477 (1988); Sanford et al., Particulate Science and Technology 5.27–37 (1987)(onion); Svab et al., Proc. Natl. Acad. Sci. USA 87.—8526–8530 (1990) (tobacco chloroplast); Christou et al., Plant Physiol 87,671–674 (1988)(soybean); McCabe et al., BioTechnology 6.923–926 (1988)(soybean); Klein et al., Proc. Natl. Acad. Sci. USA, 85:4305–4309 (1988)(maize); Klein et al., BioTechnology 6.,559–563 (1988) (maize); Klein et al., Plant PhysioL 91.,440–444 (1988) (maize); Fromm et al., BioTechnology 8:833–839 (1990); and Gordon-Kamm et al., Plant Cell 2: 603–618 (1990) (maize); Koziel et al., Biotechnology 11: 194–200 (1993) (maize); Shimamoto et al., Nature 338: 274–277 (1989) (rice); Christou et al., Biotechnology 9: 957–962 (1991) (rice); Datta et al., BioTechnology 8.736–740 (1990) (rice); European Patent Application EP 0 332 581 (orchardgrass and other Pooideae); Vasil et al., Biotechnology 11: 1553–1558 (1993) (wheat); Weeks et al., Plant Physiol. 102:1077–1084 (1993)

(wheat); Wan et al., Plant Physiol. 104:37–48 (1994) (barley); Jahne et al., Theor. Appl. Genet. 89:525–533 (1994)(barley); Umbeck et al., BioTechnology 5:263–266 (1987) (cotton); Casas et al., Proc. Natl. Acad. Sci. USA 90:11212–11216 (December 1993) (sorghum); Somers et al., BioTechnology 10:1 589–1594 (December 1992) (oat); Torbert et al., Plant Cell Reports 14:635–640 (1995) (oat); Weeks et al., Plant Physiol. 102:1077–1084 (1993) (wheat); Chang et al., WO 94/13822 (wheat) and Nehra et al., The Plant Journal 5:285–297 (1994) (wheat). A particularly preferred set of embodiments for the introduction of recombinant DNA molecules into maize by microprojectile bombardment can be found in Koziel et al., Biotechnology 11: 194–200(1993), Hill et al., Euphytica 85:119–123 (1995) and Koziel et al., Annals of the New York Academy of Sciences 792:164–171 (1996). An additional preferred embodiment is the protoplast transformation method for maize as disclosed in EP 0 292 435. Transformation of plants can be undertaken with a single DNA species or multiple DNA species (i.e. co-transformation).

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601–606). Substantial increases in transformation frequency are obtained by replacement of the recessive RRNA or r-protein antibiotic resistance genes with a dominant selectable marker, the bacterial aada gene encoding the spectinomycin-detoxifying enzyme aminoglycoside-3' adenyltransferase (Svab, Z., and Maliga, P. (1993) Proc. Natl. Acad. Sci. USA 90, 913–917). Previously, this marker had been used successfully for high-frequency transformation of the plastid genome of the green alga Chlamydomonas reinhardtii (Goldschmidt-Clermont, M. (1991) Nucl. Acids Res. 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Provisional Patent Application Ser. No. US 60/191806 filed Mar. 24, 2000, is hereby incorporated by reference.

We claim:

1. An isolated nucleic acid that encodes SEQ ID NO:4.

2. The isolated nucleic acid of claim 1 comprising SEQ ID NO: 3.

3. A transgenic monocot cell having a genome comprising a nucleic acid sequence that encodes a protein of SEQ ID NO:4.

4. A transgenic dicot cell having a genome comprising a nucleic acid sequence that encodes a protein of SEQ ID NO:4.

5. A transgenic plant with a genome comprising a nucleic acid sequence that encodes a protein of SEQ ID NO:4.

6. A transgenic plant of claim 5 wherein the plant is rice.

7. A transgenic plant of claim 5 wherein the plant is maize.

8. A transgenic plant of claim 5 wherein the plant is tobacco.

9. A transgenic plant of claim 5 wherein the plant is cotton.

10. Seed of a transgenic plant of claim 5, wherein the seed comprises the nucleic acid sequence.

11. Progeny of the seed of claim 10, wherein the progeny comprises the nucleic acid sequence.

* * * * *

UNITED STATES PATENT AND TRADEMARK OFFICE

CERTIFICATE OF CORRECTION

PATENT NO. : 6,639,129 B2 
DATED : October 28, 2003
INVENTOR(S) : Richard H. ffrench-Constant et al.

It is certified that error appears in the above-identified patent and that said Letters Patent is hereby corrected as shown below:

<u>Column 75,</u>
Lines 2 and 3, "nucleic acid" should read -- nucleic acid sequence --
Line 2, "encodes" should read -- encodes a protein comprising the amino acid sequence of --
Lines 5 and 8, "having a genome" should be deleted
Lines 6 and 9, "encodes a protein" should read -- encodes a protein comprising the amino acid sequence --
Line 11, "with a genome" should be deleted
Line 12, "protein" should read -- protein comprising the amino acid sequence --

<u>Column 76,</u>
Line 1, 2, 3 and 5, "A transgenic plant" should read -- The transgenic plant --
Line 7, "a transgenic plant" should read -- the transgenic plant --

Signed and Sealed this

Thirtieth Day of March, 2004

JON W. DUDAS
*Acting Director of the United States Patent and Trademark Office*